United States Patent [19]

Paoletti et al.

[11] Patent Number: 5,364,773
[45] Date of Patent: Nov. 15, 1994

[54] GENETICALLY ENGINEERED VACCINE STRAIN

[75] Inventors: Enzo Paoletti, Delmar; Marion E. Perkus, Altamont, both of N.Y.

[73] Assignee: Virogenetics Corporation, Troy, N.Y.

[21] Appl. No.: 36,217

[22] Filed: Mar. 24, 1993

Related U.S. Application Data

[63] Continuation of Ser. No. 666,056, Mar. 7, 1991, abandoned.

[51] Int. Cl.$^5$ .............. C12P 21/02; C12P 19/34; C12N 15/00; C12N 7/00
[52] U.S. Cl. .............. 435/69.1; 435/69.3; 435/172.3; 435/235.1; 435/236; 435/240.1; 530/300; 530/350; 424/205.1; 424/232.1; 935/32; 935/65; 935/70
[58] Field of Search .............. 435/235.1, 236, 69.1, 435/69.3, 240.1, 172.3, 91; 424/89; 536/27; 530/300, 350; 935/32, 65, 70

[56] References Cited

U.S. PATENT DOCUMENTS 5,225,336  7/1993  Paoletti .............. 435/69.1

FOREIGN PATENT DOCUMENTS

| | | |
|---|---|---|
| 78906/87 | 5/1988 | Australia . |
| 0262043 | 3/1988 | European Pat. Off. . |
| WO89/12103 | 12/1989 | WIPO . |
| 9010693 | 9/1990 | WIPO . |
| 9012101 | 10/1990 | WIPO . |

OTHER PUBLICATIONS

Turner, P. C. (90) Curr. Topics in Microbiol & Immunol. 163: 125–151.
Gallo, S. et al. (1989) Virology (73: 323–329.
Moss, B. (1991) Science 252: 1662–1667.
Rodriguez, D. et al. (1989) Proc. Natl. Acad. Sci USA 86:1287–1291.
Adamowicz, Ph., F. Tron, R. Vinas, M. N. Mevelec, I. Diaz, A. M. Courouce, M. C. Mazert, D. Lagarde and M. Girard, In Viral Hepatitis and Liver Disease, pp. 1087–1090 (1988).
Alexander, D. J. In Diseases of Poultry, 9th edition, eds. B. W. Calnek, H. J. Barnes, C. W. Beard, W. M. Reid and H. W. Yoder, Jr., (Iowa State University Press, Ames, Iowa, USA) pp. 496–519 (1991).
Alkhatib, G., C. Richardson, and S-H. Shen, Virology 175, 262–270 (1990).
Alkhatib, G. and D. Briedis, Virology 150, 479–490 (1986).
Allen, P. and Rapp, F., J. Infect. Dis. 145, 413–421 (1982).
Avery, R. J., and J. Niven., Infect. and Immun. 26, 795–801 (1979).
Baer. R., Bankie, A. T., Biggin. M. D., Deiniger. P. L., Farrel. P. J., Gibson. T. J., Hatfull. G., Hudsson. G. S., Satchwell. S. C., Seguin. C., Tuffnell. P. S., Barrell. B. G., Nature 310, 207–211 (1984).
Balachandran, N., Bacchetti, S. and Rawls. W., Infec. Immun. 37, 1132–1137 (1982).
Beard, C. W., Avian Diseases 23, 327–334 (1979).
Beard, C. W., and R. P. Hanson, In Disease of poultry, 8th edition, ed. M. S. Hofstad, (Iowa State University (List continued on next page.)

*Primary Examiner*—Joan Ellis
*Assistant Examiner*—Michael S. Tuscan
*Attorney, Agent, or Firm*—Curtis, Morris & Safford

[57] ABSTRACT

What is described is a modified vector, such as a recombinant poxvirus, particularly recombinant vaccinia virus, having enhanced safety. The modified recombinant virus has nonessential virus-encoded genetic functions inactivated therein so that virus has attenuated virulence. In one embodiment, the genetic functions are inactivated by deleting an open reading frame encoding a virulence factor. In another embodiment, the genetic functions are inactivated by insertional inactivation of an open reading frame encoding a virulence factor. What is also described is a vaccine containing the modified recombinant virus having nonessential virus-encoded genetic functions inactivated therein so that the vaccine has an increased level of safety compared to known recombinant virus vaccines.

8 Claims, 7 Drawing Sheets

OTHER PUBLICATIONS

Press, Ames, Iowa) pp. 452–470 (1984).
Beattie, E., J. Tartaglia and E. Paoletti, Virology (in press) (1991).
Ben-Porat, T. and A. S. Kaplan, In The Herpesviruses, vol. 3, ed. B. Roizman, (Plenum Publishing Corp., New York) pp. 105–173 (1985).
Ben-Porat, T., J. DeMarchi, J. Pendrys, R. A. Veach, and A. S. Kaplan, J. Virol. 57, 191–196 (1986).
Ben-Porat, T. In Organization and replication of viral DNA, ed. A. S. Kaplan, (CRC Press, Inc., Boca Raton, Fla.) pp. 147–172 (1982).
Ben-Porat, T. and A. S. Kaplan, Virology 41, 265–273 (1970).
Ben-Porat, T., F. J. Rixon, and M. L. Blankenship, Virology 95, 285–294 (1979).
Boursnell, M. E. G., I. J. Foulds, J. I. Campbell and M. M. Binns, J. Gen. Virol. 69, 2995–3003 (1988).
Boursnell, M. E. G., P. F. Green, J. I. A. Campbell, A. Deuter, R. W. Peters., F. M. Tomley, A. C. R. Samson, P. Chambers, P. T. Emmerson, and M. M. Binns, J. Gen. Virol. 71, 621–628 (1990a).
Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23, 305–316 (1990b).
Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300. (1990c).
Brandt, W. E., J Infect Dis. 157, 1105–1111 (1988).
Bryson, Y., Dillon, M., Lovett, M., Acuna, G., Taylor, S., Cherry, J., Johnson, B., Wiesmeier, E., Growdon, W., Creagh-Kirk, T. and Keeney, R., N. Engl. J. Med. 308, 916–921 (1983).
Bucher, D., Popplo, S., Baer, M., Mikhail, A., Gong, Y-F., Whitaker, C., Paoletti, E., and Judd, A., J. Virol. 63, 3622–3633 (1989).
Buller, R. M. L., S. Chakrabarti, J. A. Cooper, D. R. Twardzik and B. Moss, J. Virol. 62, 866–874 (1988).
Bunn, T. O., In Rabies, eds. Campbell, J. B. and Charlton K. M. (Kluwer Academy Press, Boston) pp. 474–491 (1988).
Cantin, E., Eberle, R., Baldrick, J., Moss, B., Willey, D., Notkins, A. and Openshaw, H., Proc. Natl. Acad. Sci. USA, 84, 5908–5912 (1987).

Chakrabarti, S., Robert-Guroff, M., Wong-Staal, F., Gallo, R. C., and Moss, B. Nature 320, 535–537 (1986).
Chambers, P., N. S. Millar, and P. T. Emmerson, J. Gen. Virol. 67, 2685–2694 (1986).
Chambers, T. M., Y. Kawaoka, and R. G. Webster, Virology 167, 414–421 (1988).
Chan, W., Immunol. 49, 343–352 (1983).
Chen, C., R. W. Coupans, and P. W. Choppin, J. Gen. Virol. 11, 53–58 (1971).
Cheng, K-C, G. L. Smith and B. Moss, J. Virol. 60, 337–344 (1986).
Chisari, F. V., P. Filippi, A. McLachlan, D. R. Milich, M. Riggs, S. Lee, R. R. Palmiter, C. A. Pinkert and R. L. Brinster, J. Virol. 60, 880–887 (1986).
Cianciolo, G. J., Copeland T. D., Oroszlan S., Snyderman, R., Science 230, 453–45 (1985).
Clarke, B. E., S. E. Newton, A. R. Carroll, M. J. Francis, G. Appleyard, A. D. Syred, P. E. Highfield, D. J. Rowlands and F. Brown, Nature 330, 381–384 (1987).
Cox, J. H., B. Dietzschold, and L. G. Schneider, Infect. Immun. 16: 754–759 (1977).
Davis, W., Taylor, J. and Oakes, J., J. Infect. Dis. 140, 534–540 (1979).
De, B. K., M. W. Shaw, P. A. Rota, M. W. Harmon, J. J. Esposito, R. Rott, N. J. Cox and A. P. Kendal, Vaccine 6, 257–261 (1988).
Delpeyroux, F., N. Peillon, B. Blondel, R. Crainic and R. E. Streeck, J. Virol., 62, 1836–1839 (1988).
Derosiers, R. C., M. S. Wyand, T. Kodama, T. J. Ringler, L. O. Arthur, P. K. Sehgal, N. L. Letvin, N. W. King and M. D. Daniel, Proc. Natl. Acad. Sci. USA 86, 6353–6357 (1989).
Diallo, A., Vet. Micro. 23, 155–163 (1990).
Douglas, J., Critchlow, C., Benedetti, J., Mertz, G., Connor, J., Hintz, M., Fahnlander, A., Remington, M., Winter, C. and Corey, L., N. Engl. J. Med. 310, 1551–1556 (1984).
Dowbenko, D. and Lasky, L., J. Virol. 52, 154–163 (1984).
Dowling, P. C., B. M. Blumberg, J. Menonna, J. E. Adamus, P. Cook, J. C. Crowley, D. Kolakofsky, and S. D. Cook, J. Gen. Virol. 67, 1987–1992 (1986).
Dreyfuss, G., Adam, S. A., and Choi, Y.-D., Mol. Cell. Biol. 4, 415–423 (1984).
Drillien, R., R. Spehner, A. Kirn, P. Giraudon, R.

(List continued on next page.)

OTHER PUBLICATIONS

Buckland, F. Wild, and J. P. Lecocq, Proc. Natl. Acad. Sci. USA 85, 1252–1256 (1988).

Eble, B. E., V. R. Lingappa and D. Ganem, Mol. Cell. Biol. 6, 1454–1463 (1986).

Espion, D., S. de Henau, C. Letellier, C.-D. Wemers, R. Brasseur, J. F. Young, M. Gross, M. Rosenberg, G. Meulemans and A. Burny. Arch. Virol. 95, 79–95 (1987).

Esposito, J. J., K. Brechling, G. Baer and B. Moss, Virus Genes 1 7–21 (1987).

Esposito, J. J., J. C. Knight, J. H. Schaddock, F. J. Novembre and G. Baer, Virology 165, 313–316 (1988).

Falgout, B., Chanock, R. and Lai, C.-J. J. Virology 63, 1852–1860 (1989).

Falkner, F. G. and B. Moss, J. Virol. 64, 3108–3111 (1990).

Franchini, G., K. A., Giomnini, F., Jagodzinski, L., DeRossi, A., Bosch, M., Biberfield, G., Fenyo, E. M., Albert, J., Gallo, R. C., and Wong-Staal, F., Proc. Natl. Acad. Sci. USA 86, 2433–2437 (1989).

Franchini, G., Gurgo, C., Guo, H.-G., Gallo, R. C., Collati, E., Fargnoli, K. A., Hall, L. F., Wong-Staal, F., and Reitz, Jr., M. S., Nature (London) 328, 539–543 (1987).

Galibert, F., E. Mandart, F, Fitoussi, P. Tiollais and P. Charnay, Nature 281, 646–650 (1979).

Garten, W., Kohama, T., and H-D. Klenk. J. Gen. Virol. 51, 207–211 (1980).

Gibson, C. A., Schlesinger, J. J., and Barrett, A. D. T., Vaccine 6, 7–9 (1988).

Gould, E. A., Buckley, A., Barrett, A. D. T., and Cammack, N., J. Gen. Virol. 67, 591–595 (1986).

Graves, M. C., J. M. Silver, and P. W. Choppin, Virology 86, 254–263 (1978).

Hampl, H., Ben-Porat, T., Ehrlicher, L., Habermehl, K.,-O., and Kaplan, A. S., J. Virol. 52, 583–590 (1984).

Heermann, K. H., U. Goldmann, W. Schwartz, T. Seyfarth, H. Baumgarten and W. H. Gerlich, J. Virol. 52, 396–402 (1984).

Henchal, E. A., Henchal, L. S., and Schlessinger, J. J., J. Gen. Virol. 69, 2101–2107 (1988).

Hinshaw, V. S., R. G. Webster, W. J. Bean, G. Sriram, Comp. Immunol. Microbiol. Infect. Dis. 3, 155–164 (1981).

Hoffar, O., Garrigues, J., Travis, B., Moran, P., Zarling, J. and Hu, S.-L., J. Virol. 64, 2653–2659, (1990).

Homma, M., and M. Ohuchi, J. Virol. 12, 1457–1465 (1973).

Hu, S.-L., Travis, B. M., Garrigues, J., Zarling, J. M., Eichberg, J. W. and Alpers, C. E., In Vaccine 90, eds. Chanock, R. M., Lerner, R. A., Brown, F., and Ginsberg, H., (Cold Spring Harbor Press, Cold Spring Harbor, N.Y.) pp. 231–236 (1990).

Hu, S.-L., Kosowski, S. and Dalrymple, J., Nature 320, 535–537 (1986).

Huang, C. H., Advances in Virus Research 27, 71–101 (1982).

Hunt, L. A., D. W., Brown, H. L. Robinson, C. W. Naeve, and R. G. Webster, J. Virol. 62, 3014–3019 (1988).

Itoh, Y., E. Takai, H. Ohnuma, K. Kitajima, F. Tsuda, A. Machida, S. Mishiro, T. Nakamura, Y. Miyakawa and M. Mayumi, Proc. Natl. Acad. Sci. USA 83, 9174–9178 (1986).

Javeherian, K., Langlois, A. J., McDanal, C., Ross, K. L., Eckler, L. I., Jellib, C. L., Profy, A. T., Rusche, J. R., Bolognesi, D. P., Putney, S. D., and Mathews, T. J., Proc. Natl. Acad. Sci. USA 86, 6768–6772 (1989).

Jilg, W., C. Delhoune, F. Deinhardt, A. J. Roumeliotou-Karayannis, G. J. Papaevangelou, I. K. Mushahwar and L. R. Overby, J. Med. Virol. 13, 171–178 (1984).

Karacostas, V., Nagashima, K., Gonda, M. A., and Moss, B., Proc. Natl. Adad. Sci, USA 86, 8964–8968 (1989).

Kaufman, B. M., Summers, P. L., Dubois, D. R., Cohen, W. H., Gentry, M. I., Timchak, R. L., Burke, D. S. and Eckels, K. H., Am. J. Trop. Med. Hyg. 41, 576–580 (1989).

Kaufman, B. M., Summers, P. L., Dubois, D. R., and Eckels, K. H., Am. J Trop. Med. Hyg. 36, 427–434 (1987).

Kieff, E., and Liebowitz, D., In Virology, Second Edition, eds. B. N. Fields, D. M. Knipe et al., (Raven Press) (1990).

Kieny, M. P., R. Lathe, R. Drillien, D. Spehner, S. Skory, D. Schmitt, T. Wiktor, H. Koprowski and J. P. Lecocq, Nature (London) 312, 163–166 (1984).

Killington, R. A., J. Yeo, R. W. Honess, D. H. Watson, B. E. Duncan, I. W. Halliburton, and J. Mumford, J. gen. Virol. 37, 297–310 (1977).

(List continued on next page.)

OTHER PUBLICATIONS

Kimura-Kuroda, J., and Yasui, K., Immunol. 141, 3606–3610 (1988).

Kingsbury, D. W., M. A. Bratt, P. W. Choppin, R. P. Hanson, T. Hosaka, Y. ter Meulen, E. Norrby, W. Plowright, R. Rott and W. H. Wunner, Intervirology 10, 137–152 (1978).

Kingsbury, D. W., In Virology, Second Edition, eds. B. N. Fields, D. M. Knipe et al., (Raven Press, Ltd. New York) pp. 1075–1089 (1990).

Klasse, P. J., Pipkorn, R., and Blomberg, J., Proc. Natl. Acad. Sci. USA 85, 5225–5229 (1988).

Kodama, T., Wooley, D. P., Naidu, Y. M., Kestler III, H. W., Daniel, M. D., Li, Y. and Derosiers, R. C. J. Virol. 63, 4709–4714 (1989).

Koff, W. C. and Fauci, A. S., AIDS 1, 5125–5129 (1989).

Kost, T. A., E. V. Jones, K. M. Smith, A. P. Reed, A. L. Brown, and T. J. Miller, Virology 171, 365–376 (1989).

Koup, R. A., Sullivan, J. L., Levine, P. H., Brettler, D., Mahr, A., Mazzara, G., McKenzie, S., and Panicali, D. Blood 73, 1909–1919 (1989).

Kunkel, T. A., Proc. Natl. Acad. Sci. USA 82, 488–492 (1985).

Kunkel, T. A., Roberts, J. D., and Zakour, R. A., Method in Enzym. 154, 367–382 (1987).

Kuroda, K., C. Hauser, R. Rott, H.-D. Klenk, and W. Doerfler, EMBO 5, 1359–1365 (1986).

Kuroki, K., R. Russnak and D. Ganem, Mol. Cell. Biol. 9, 4459–4466 (1989).

Laemmli, U. K., Nature (London) 227, 680–685 (1970).

Lane, J. M., Ruben, F. L., Neff, J. M., and Millar, J. D., New Eng. J. Med. 281, 1201–1208 (1969).

Lathe, R., M. P. Kieny, D. Schmitt, P. Curtis and J. P. Lecocq, J. Mol. Appl. Gen. 2, 331–342 (1984).

Le, L., R. Brasseur, C. Wemers, G. Meulemans, and A. Burny, Virus Genes 1, 333–350 (1988).

Lecocq, J. P., M. Zukowski and R. Lathe, In Methods in Virology, eds. Maramorosch, K. and Koprowski, H., (Academic Press, New York) vol. VII, 124–172 (1984).

Lecocq, J. P., M. P. Kieny, Y. Lemoine, R. Drillien, T. Wiktor, H. Koprowski and R. Lathe, In World's Debt to Pasteur, eds. Koprowski, H. and Plotkin, S. A., (Alan R. Liss, New York), 259–271 (1985).

Lukacs, N., Theil, H.,-J., Mettenleiter, T. C., and Rziha, H.,-J.,J. Virol. 53, 166–172 (1985).

Macfarlan, R. I., B. Dietzschold, and H. Koprowski, J. Mol. Immunol. 23, 733–741 (1986).

Marsden, H., Stow, N., Preston, V., Timbury, M. and Wilkie, N., J. Virol. 28, 624–642 (1978).

Marsden, H., Buckmaster, A., Palfreyman, J., Hope, R. and Minson, A., J. Virol. 50, 547–554 (1984).

Mason, P. W., Dalrymple, J. M., Gentry, M. K., McCown, J. M., Hoke, C. H., Burke, D. S., Fournier, M. J., and Mason, T. L., J Gen. Virol. 70, 2037–2049 (1989).

Mason, P. W., McAda, P. C., Dalrymple, J. M., and Mason, T. L., Virology 158, 361–372 (1987a).

Mason, P. W., McAda, P. W., Mason, T. L., and Fournier, M. J., Virol. 161, 262–267 (1987b).

Mason, P. W., Pincus, S., Fournier, M. J., Mason, T. L., Shope, R. E., and Paoletti, E., Virol. 180, 294–305 (1991).

Mason, P. W., Virol. 169, 354–364 (1989).

Matthews, R. E. F., Intervirology 17, 104–105 (1982a).

Matthews, R. E. F., Intervirology 17, 42–44 (1982b).

McAda, P. C., Mason, P. W., Schmaljohn, C. S., Dalrymple, J. M., Mason, T. L. and Fournier, M. J. Virology 158, 348–360 (1987).

McGinnes, L. W., and T. G. Morrison, Virus Research 5, 343–356 (1986).

McLachlan, A., D. R. Milich, A. K. Raney, M. G. Riggs, J. L. Hughes, J. Sorge and F. V. Chisari, J. Virol. 61, 683–692 (1987).

McLaughlin-Taylor, E., Willey, D., Cantin, E., Eberle, R., Moss, B. and Openshaw H., J. Gen. Virol. 69, 1731–1734 (1988).

McGeoch, D., Moss, H., McNab, D. and Frame, M., J. Gen. Virol. 68, 19–38 (1987).

Meignier, B., Jourdier, T., Norrild, B., Pereira, L. and Roizman, B., J. Infect. Dis. 155, 921–930 (1987).

Merz, D. C., A. Scheid, and P. Choppin, J. Exper. Med. 151, 275–288 (1980).

Mettenleiter, T. C., N. Lukacs, H.-J. Thiel, C. Schreurs, and H.-J. Rziha, Virology 152, 66–75 (1986).

Mettenleiter, T. C., N. Lukacs, and H.-J. Rziha, J. Virol. 53, 52–57 (1985).

Meulemans, G., C. Letellier, M. Gonze, M. C. Carlier, and A. Burny, Avian Pathol. 17, 821–827 (1988).

(List continued on next page.)

OTHER PUBLICATIONS

Michel, F., Hoffenbach, A., Langlade-Demoyen, P., Guy, B., Lococq, J.-P., Wain-Hobson, S., Kieny, M.-P. and Plata, F., Eur. J. Immunology 18, 1917 (1988).

Milich, D. R. and A. McLachlan, In Viral Hepatitis and Liver Disease, pp. 645–649 (1988).

Milich, D. R., G. B. Thornton, A. R. Neurath, S. B. Kent, M-L. Michel, P. Tiollais and F. V. Chisari, Science 228, 1195–1199 (1985).

Milich, D. R., A. McLachlan, A. Moriarty and G. B. Thornton, J. Immun. 138, 4457–4465 (1987a).

Milich, D. R., A. McLachlan, G. B. Thornton and J. L. Hughes, Nature 329, 547–549 (1987b).

Milich, D. R., A. McLachlan, F. V. Chisari, S. B. H. Kent and G. B. Thornton, J. Immun. 137, 315–322 (1986).

Miller, G., In Virology, Second Edition, eds. B. N., Fields, D. M. Knipe et al., (Raven Press) (1990).

Monath, T. P., In The Togaviridae and Flaviviridae, eds. S. Schlesinger and M. J. Schlesinger, (Plenum Press, New York/London) pp. 375–440 (1986).

Morgan, J. R. and B. E. Roberts, J. Virol. 51, 283–297 (1984).

Moss, B., G. L. Smith, J. L. Gerin and R. H. Purcell, Nature 311, 67–69 (1984).

Murphy, B. R. and R. G. Webster, In Virology, Second Edition, eds. B. N. Fields, D. M. Knipe et al., (Raven Press, Ltd., New York) pp. 1091–1152 (1990).

Murphy-Corb, M., Martin, L. N., Davison-Fairburn, B., Montelaro, R. C., Miller, M., Ohkawa, S., Baskin, G. B., Zhang, J.-Y., Putney, S. D., Allison, A. C. and Eppstein, D. A., Science 246, 1293–1297 (1989).

Murray, K., S. A. Bruce, A. Hinnen, P. Wingfield, P. M. C. A. van Erd, A. de Reus and H. Schellekens, EMBO 3, 645–650 (1984).

Nagai, Y., H. D. Klenk, and R. Rott, Virology 72, 494–508 (1976).

Nagai, Y., T. Yoshida, M. Hamaguchi, H. Naruse, M. Iinuma, K. Maeno, and T. Matsumoto, Microbiol. Immunol. 24, 173–177 (1980).

Neurath, A. R., B. A. Jameson and T. Huima, Microbiological Sciences 4, 45–51 (1987).

Neurath, A. R., and S. B. H. Kent, Adv. Vir. Res. 34, 65–142 (1988).

Neurath, A. R., S. B. H. Kent and N. Strick, Science 224, 392–395 (1984).

Neurath, A. R., S. B. H. Kent, N. Strick and K. Parker, Cell 46, 429–436 (1986).

Neurath, A. R., N. Strick and M. Girard, Mol. Immun. 26, 53–62 (1989).

Nixon, D. F., Townsend, A. R. M., Elvin, J. G., Rizza, C. R., Gallwey, J. and McMichael, A. J., Nature 326, 484–487 (1988).

Norrby, E., and Y. Gollmar, Infect. and Immun. 11, 231–239 (1975).

Norrby, E., S. N. Chen, T. Togashi, H. Shesberadaran, and K. P. Johnson, Archives of Virology 71, 1–11 (1982).

Norrby, E., and M. N. Oxman, In Fields Virology, 2nd Edition, eds. B. N. Fields and D. M. Knipe, (Raven Press), NY) pp. 1013–1044 (1990).

Oakes, J. and Rosemond-Hornbeak, H., Infect. Immun. 21, 489–495 (1978).

Oakes, J., Davis, W., Taylor, J. and Weppner, W., Infect. Immun. 29, 642–649 (1980).

Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).

Ono, Y., H. Onda, R. Sasada, K. Igarashi, Y. Sugino and K. Nishioka, Nuc. Acids Res. 11, 1747–1757 (1983).

Ou, J.-H. and W. J. Rutter, J. Virol. 61, 782–786 (1987).

Paoletti, E., B. Lipinskas, C. Samsonoff, S. Mercer and D. Panicali, Proc. Natl. Acad. Sci. USA 81, 193–197 (1984).

Petrovskis, E. A., J. G. Timmins, and L. E. Post, J. Virol. 60, 185–193 (1986a).

Petrovskis, E. A., Timmins, J. G., Armentrout, M. A., Marchioli, C. C., Yancey, Jr., R. J., Post, L. E., J. Virol. 59, 216–223 (1986b).

Plata, F., Autran, B., Martins, L. P., Wain-Hobson, S., Raphael, M., Mayaud, C., Denis, M., Guillon, J.-M., Debre, P., Nature 328, 348–351 (1987).

Pontisso, P., M-A. Petit, M. J. Bankowski and M. E. Peeples, J. Virol. 63, 1981–1988 (1989).

Portetelle, D., Limbach, K., Burny, A., Mammerickx, M., Desmetttre, P., Riviere, M., Zavada, J. and Paoletti, E. Vaccine 9, 194–200 (1991).

Powell, K. and Watson, D. J., Gen. Virol. 29, 167–178 (1975).

Pratt, D. and S. Subramani, Nuc. Acids Res. 11, 8817–8823 (1983).

Prevec, L., J. B. Campbell, B. S. Christie, L. Belbek, and F. L. Graham, J. Infect. Dis. 161, 27–30 (1990).

(List continued on next page.)

OTHER PUBLICATIONS

Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, Jr., S. R., Pearson, M. L., Lautenberger, J. A., Papas, T. S., Ghrayeb, J., Chang, N. T., Gallo., R. C., and Wong-Staal F., Nature 313, 277–284 (1985).

Rautmann, G., Kieny, M. P., Brandely, R., Dott, K., Girard, M., Montagnier, L., and Lecocq, J.-P., AIDS Research and Human Retroviruses 5, 147–157 (1989).

Rea, T. J., J. G. Timmins, G. W. Long, and L. E. Post, J. Virol. 54, 21–29 (1985).

Rice, C. M., Lenches, E. M., Eddy, S. R., Shin, S. J., Sheets, R. L., and Strauss, J. H., Science 229, 726–733 (1985).

Rice, C. M., Strauss, E. G., and Strauss, J. H., In The Togaviridae and Flaviviridae, eds. S. Schlesinger and M. J. Schlesinger, (Plenum Press, New York/London) pp. 279–326 (1986).

Richardson, C., D. Hull, P. Greer, K. Hasel, A. Berkovich, G. Englund, W. Bellini, B. Rima, and R. Lazzarini, Virology 155, 508–523 (1986).

Richardson, C. D., A. Berkovich, S. Rozenblatt, and W. Bellini, J. Virol. 54, 186–193 (1985).

Riviere, Y., Tanneau-Salvadori, F., Regnault, A., Lopez, O., Sansonetti, P., Guy, B., Kieny, M.-P., Fournel, J.-J. and Montagnier, L., J. Virol. 63, 2270–2277 (1989).

Robbins, A. K., R. J. Watson, M. E. Whealy, W. W. Hays, and L. W. Enquist, J. Virol. 58, 339–347 (1986a).

Robbins, A. K., Watson, R. J., Whealy, M. A. Harp, W. W., and Enquist, L. W., J. Virol. 60, 436–449 (1986b).

Robbins, A. K., J. H. Weis, L. W. Enquist, and R. J. Watson, J. Mol. Appl. Genet. 2, 485–496 (1984).

Robbins, A. K., Dorney, D. J., Wathen, M. W., Whealy, M. E., Gold, C., Watson, R. J., Holland, L. E., Weed, S. D., Levine, M., Glorioso, J. C., and Enquist, L. W., J. Virol. 61, 2691–2701 (1987).

Roizman, B. and Sears, A., In Virology, eds. Fields, B. and Knipe, D., (Raven Press, Ltd.) pp. 1795–1841 (1990).

Rubenstein, A. S. and A. S. Kaplan, Virology 66, 385–392 (1975).

Ruegg, C. L., Monell, C. R., and Strand, M., J. Virol. 63, 3250–3256 (1989a).

Ruegg, C. L., Monell, C. R., and Strand M., J. Virol. 63, 3257–3260 (1989b).

Saiki, R. K., Gelfand, D. H., Stoffel, S. Scharf, S. J., Higuihi, R., Horn, G. T., Mullis, K. B., Erlich, H. A., Science 239, 487–491 (1988).

Sanchez-Pescador, R., Power, M. D., Barr, P. J., Steimer, K. S., Stempien, M. M., Brown-Shimer, S. L., Gee, W., Renard, A., Randolph, A., Levy, J. A., Dina, D., and Luciw, P. A., Science 227, 484–492 (1985).

Scheid, A., and P. W. Choppin, Virology 57, 475–490 (1974).

Scheid, A., L. A. Caliguiri, R. W. Compans, and P. W. Choppin, Virology 50, 640–652 (1972).

Schlesinger, J. J., Brandriss, M. W., Cropp, C. B., and Monath, T. P., J. Virol. 60, 1153–1155 (1986).

Schlesinger, J. J., Brandriss, M. W., and Walsh, E. E., J. Immunol. 135, 2805–2809 (1985).

Schlesinger, J. J., Brabdriss, M. W., and Walsh, E. E., J Gen. Virol. 68, 853–857 (1987).

Schlicht, H-J. and H. Schaller, J. Virol. 63, 5399–5404 (1989).

Shafferman, A., Lennox, J., Grosfeld, H., Sadoff, J., Redfield, R. R., and Burke, D. S., AIDS Research and Human Retroviruses 5, 33–39 (1989).

Shioda, T. and H. Shibuta, Virology 175, 139–148 (1990).

Shope, R. E., In The Togaviruses, ed. R. W. Schlesinger, (Academic Press, New York) pp. 47–82 (1980).

Slabaugh, M. B. and N. A. Roseman, Proc. Natl. Acad. Sci. USA 86, 4152–4155 (1989).

Smith, G. L. and Y. Sang Chan, J. Gen. Virol. 72, 511–518 (1991).

Smith, G. L., M. Mackett and B. Moss, Nature 302, 490–495 (1983).

Smith, J. S., P. A. Yager and G. M. Baer, In Laboratory Techniques in Rabies, eds. M. M. Kaplan and H. Koprowski (WHO Geneva) pp. 354–357 (1973).

Spear, P., In Herpesviruses, vol. 3, ed. Roizman, B. (Plenum, NY) pp. 315–356 (1984).

Spehner, D., R. Drillien, and J. P. Lecocq, J. Virol. 64, 527–533 (1990).

Stahl, S. J. and K. Murray, Proc. Natl. Acad. Sci. USA 86, 6283–6287 (1989).

Starcich et al., Cell 45, 637–648 (1986).

(List continued on next page.)

OTHER PUBLICATIONS

Stevely, W. S., J. Virol. 22, 232–234 (1977).
Stuve, L., Brown–Shimer, S., Pachl, C., Najarian, R., Dina, D. and Burke, R., J. Virol. 61, 326–335 (1987).
Tartaglia, J. and Paoletti, E., In Immunochemistry of viruses, II, eds. van Regenmortel, M. H. V. and Neurath, A. R., (Elsevier Science Publishers B.V., Amsterdam) p. 125 (1990b).
Taylor, J., C. Edbauer, A. Rey-Senelonge, J. F. Bouquet, E. Norton, S. Goebel, P. Desmettre and E. Paoletti, J. Virol. 64, 1441–1450 (1990).
Taylor, J., C. Trimarchi, R. Weinberg, B. Languet, F. Guillemin, P. Desmettre and E. Paoletti, Vaccine 9, 190–193 (1991b).
Taylor, J., S. Pincus, J. Tartaglia, C. Richardson, G. Alkhatib, D. Briedis, M. Appel, E. Norton and E. Paoletti, J. Virology 65 in press Aug. (1991c).
Thornton, G. B., D. Milich, F. Chisari, K. Mitamura, S. B. Kent, R. Neurath, R. Purcell and J. Gerin, In Vaccines 87, (Cold Spring Harbor, N.Y.) (1987).
Wild, T. F., E. Malvoisin, and R. Buckland, J. Gen. Virol. 72, 439–447 (1991b).
Tomley, F., Vaccine 9, 4–5 (1991).
Toyoda, T., T. Sakaguchi, K. Imai, N. M. Inocencio, B. Gotoh, M. Hamaguchi, and Y. Nagai, Virology 158, 242–247 (1987).
Ueda, Y., S. Morikawa and Y. Matsuura, Virology 177, 588–594 (1990).
Valenzuela, P., P. Gray, M. Quiroga, J. Zaldivar, H. M. Goodman and W. J. Rutter, Nature 280, 815–819 (1979).
Valenzuela, P., A. Medina, W. J. Rutter, G. Ammerer and B. D. Hall, Nature 298, 347–350 (1982).
Valenzuela, P., D. Coit, M. A. Medina-Selby, C. H. Kuo, G. V. Nest, R. L. Burke, P. Bull, M. S. Urdea and P. V. Graves, Bio/Technology 3, 323–326 (1985).
Vialard, J., M. Lalumiere, T. Vernet, D. Briedis, G. Alkhatib, D. Levin, and C. Richardson, J. Virol. 64, 37–50 (1990).
Vos, J. C. and Stunnenberg, H. G., EMBO J. 7, 3487–3492 (1988).
Wachsman, M., Aurelian, L., Smith, C., Lipinskas, B., Perkus, M. and Paoletti, E., J. Infect. Dis. 155, 1188–1197 (1987).
Walker, B. D., Flexner, C., Birch-Limberger, K., Fisher, L., Paradis, T. J., Aldovini, A., Young, R., Moss, B., and Schooley, R. T., Proc. Natl. Acad. Sci. 86, 9514–9519 (1989).
Walker, B. D., Flexner, C., Paradis, T. J., Fuller, T. C., Hirsch, M. S., Schooley, R. T. and Moss, B., Science 240, 64–66 (1988).
Walker, B. D., Chakrabarti, S., Moss, B., Paradi, T. J., Flynn, T., Durno, A. G., Blumberg, R. S., Kaplan, J. C., Hirsch, M. S., and Schooley, R. T., Nature 328, 345–348 (1987).
Wathen, M. W. and Wathen, L. M. K., J. Virol. 51, 57–62 (1984).
Watson, R., Gene 26, 307–312 (1983).
Weir, J., Bennett, M., Allen, E., Elkins, K., Martin, S. and Rouse, B., J. Gen. Virol. 70, 2587–2594 (1989).
Weiss, R. A., Clapham, P. R., Cheingsong-Popov, R., Dalgleish, G., Carne, C. A. Weller, I. V., and Tedder, R. S., Nature 316, 69–72 (1985).
Wengler, G., and Wengler, G., J. Virol. 63, 2521–2526 (1989a).
Wengler, G., and Wengler, G., J. Gen. Virol. 70, 987–992 (1989b).
Wiktor, T. J., E. Gyorgy, H. D. Schlumberger, F. Sokol and H. Koprowski, J. Immunol. 110, 269–276 (1973).
Wiktor, T. J., Dev. Biol. Stand 40, 255–264 (1977).
Wiktor, T. J., R. I. Macfarlan, K. J. Reagan, B. Dietzschold, P. J. Curtis, W. H. Wunner, M. P. Kieny, R. Lathe, J. P. Lecocq, M. Mackett, B. Moss and H. Koprowski, Proc. Natl. Acad. Sci. USA 81, 7194–7198 (1984).
Wiktor, T. J., S. A. Plotkin and H. Koprowski, In Vaccines, eds. Plotkin S. A. and E. A. Mortimer (W. B. Saunders, Philadelphia), 474–491 (1988).
Wild, F., P. Giraudon, D. Spehner, R. Drillien, and J-P. Lecocq, Vaccine 8, 441–442 (1991a).
Winkler, G., Randolph, V. B., Cleaves, G. R., Ryan, T. E., and Stollar, V., Virol 162, 187–196 (1988).
Wittmann, G. and Rziha, H.-J. Aujeszky's disease (pseudorabies) in pigs, In Herpesvirus Diseases of Cattle, Horses and Pigs, ed Wittmann, G., (Kluwer Academic Publishers), 230–325 (1989).
Wunner, W. H., B. Dietzschold, P. J. Curtis and T. J. Wiktor, J. Gen. Virol. 64, 1649–1650 (1983).
Yelverton, E., S. Norton, J. F. Obijeski and D. V. Goeddel, Science 219, 614–620 (1983).

(List continued on next page.)

OTHER PUBLICATIONS

Yuen, L., and Moss, B., Proc. Natl. Acad. Sci. USA 84, 6417–6421 (1987).

Zagury, D., Bernard, J., Cheynier, R., Desportes, I., Leonard, R., Fouchard, I., Reveil, B., Ittele, D., Lurhuma, Z., Mbayo, K., Wane, J., Salaun, J.-J., Goussard, B., Dechazal, L., Burny, A., Nara, P. and Gallo, R. C., Nature 332, 728–731 (1988).

Zanetti, A. R., E. Tanzi, L. Ramano, P. Vigano, A. Cargnel, S. Hojvat and A. J. Zuckerman, J. Med. Virol. 32, 219–224 (1990).

Zarling, J. M., Morton, W., Moran, P. A., McClure, J., Kosowski, S. G. and Hu, S.-L., Nature 323, 344–346 (1986).

Zweig, M., Showalter, S., Bladen, S., Heilman, C. and Hampar, B., J. Virol. 47, 185–192 (1983).

Alp, N. J., T. D. Allport, J. Van Zanken, B. Rodgers, J. G. P. Sissons, and L. K. Borysiewicz, J. Virol. 65, 4812–4820.

Arikawa, J., Schmaljohn, A. L., Dalrymple, J. M., and Schmaljohn, C. S., J. Gen. Virology 70, 615–624 (1989).

Asada, H., Tamura, M., Kondo, K., Dohi, Y., Yamanishi, K., J. Gen Virology 69, 2179–2188 (1988).

Asada, H. M., Tamura, K., Kondo, Y., Okano, Y., Takahashi, Y., Dohi, T., Nagai, T., Kurata, T., and Yamanishi, K., J. Gen. Virology 68, 1961–1969 (1987).

Baxby, D. In Jenner's Smallpox Vaccine, (Heinemann Educational Books, Ltd., London) p. 214 (1981).

Baxby, D., Paoletti, E., Vaccine 9, 8–9 (1992).

Berns, K. I., In: Fields Virology, eds. B. N. Fields and D. M. Knipe, (Raven Press, New York) pp. 1743–1763 (1990).

Bishop, D. H. L., In: Bunyaviridae and Their Replication in Virology: 2nd Edition, pp. 1155–1173 (1990).

Borysiewicz, L. K., J. K. Hickling, S. Graham, J. Sinclair, M. P. Crange, G. L. Smith, and J. G. Sissons, J. Exp. Med. 168, 919–931 (1988).

Brochier, B., Kieny, M. P., Costy, F., et al., Nature, 354 520–522 (1991). Buller, R. M. L., and Palumbo, G. J., Microbiol. Rev. 55, 80–122 (1991).

Chakrabarti, S., Brechling, K., and Moss, B., Mol. Cell. Biol. 5, 3403–3409 (1985).

Chambers, T. J., Hahn, C. S., Galler, R., and Rice, C. M., Ann. Rev. Microbiol. 44, 649–688 (1990).

Charles, I. G., Rodgers, B. C., Makoff, A. J., Chatfield, S. N., Slater, D. E., and Fairweather, N. F., Infect, Immun. 59, 1627–1632 (1991).

Chirgwin, J. M., Przybyla, A. E., MacDonald, R. J., and Rutter, W. J., Biochemistry 18, 5294–5299 (1979).

Clark, N. Kushner, B. S., Barrett, M. S., Kensil, C. R., Salsbury, D., and Cotter, S., JAVMA 199, 1433–1442 (1991).

Clarke D. H., and Casals J. Am., J. Trop. Med. Hyg. 7 561–573 (1958).

Collett, M. S., Keegan, K., Hu, S.-L., Sridhar, P., Purchio, A. F., Ennis, W. H., and Dalrymple, J. M., In: The Biology of Negative Strand Viruses, pp. 321–329 (1987).

Collins P. L., Purcell, R. H., London, W. T. et al., Vaccine 8, 154–168 (1990).

Cooney, E. L., Corrier, A. C., Greenberg, P. D., et al., Lancet 337 567–572 (1991).

Dales, S., Ann. Rev. Microbiol. 44, 173–192 (1990).

Daniels, R. S., Skehel, J. J., and Wiley, D. C., J. Gen. Virol. 66, 457–464 (1985).

Dantas, J. R., Fr., Okuno, Y., Asada, H., Tamura, M., Takahashi, M., Tanishita, O., Takahashi, Y. Kurata, T., and Yamanishi, K., Virology 151, 379–384 (1986).

DeNoronha, F., Schafer, W., and Essex, M., Virology 85, 617–621 (1978).

Eisel, U., Jarausch, W., Goretzki, K., Henschen, A., Engels, J., Weller, E., Hudel, M., Habermann, E., and Niemann, H. EMBO J. 5, 2495–2502 (1986).

Elder, J. H., McGee, J. S., Munson, M., Houghton, R. A., Kloetzer, W., Bittle, J. L., and Grant, C. K., J. Virol. 61, 8–15 (1987).

Elder, J. H., and Mullens, J. V., J. Virol. 46, 871–880 (1983).

Etinger, H. M., Altenburger, W., Vaccine 1991, 9, 470–472.

Fairweather, N. F., and Lyness, V. A. *Nucleic Acids Res.* 14, 7809–7812 (1986).

Fenner, F., Wittek, R., and Dumbell, K. R., (Academic Press, Inc., San Diego, Calif.) p. 432 (1989).

Fenner, F., Virology 5, 502–529 (1958).

Flexner, C., Hugen, A., and Moss, B., Nature 330, 259–262 (1987).

Fujisaki, Y., Sugimori, T., Morimoto, T., Muira, Y., Kawakani, Y. and Nakano, K., Natl. Inst. Anim. Health Q. 15, 55–60 (1975b).

(List continued on next page.)

OTHER PUBLICATIONS

Ghendon, Y. Z., and Chernos, V. I., Acta Virol. 8, 359–368 (1964).

Giavedoni, L., Jones, L., Mebus, C., and Yilma, T. A., Proc. Natl. Acad. Sci. USA 88, 8011–8015 (1991).

Glosser, J. W., Environmental assessment and preliminary finding of NO significant impact. Veterinary biologics authorized field trial of an experimental biologic: The Wistar Institute of Anatomy and Biology proposed field trial of a live experimental vaccine vectored rabies vaccine. United States Department of Agriculture, Animal, and Plant Health Inspection Services (1989).

Gonczol, E., Furlini, G., Ianocone, J., and Plotkin, S. A., J. Virol. 14, 37–41 (1986).

Gonczol, E., C. de Taisne, G. Hirka, K. Berensci, W. Lin, E. Paoletti, and S. Plotkin, Vaccine 9, 631–637 (1991).

Gonzolez-Scarano, F., Shope, R. E., Calisher, C. H., and Nathanson, N., Virology, 120, 42–53 (1982).

Gretch, D. R., B. Kari, L. Rasmussen, R. C. Gehrz, and M. F. Stinski, J. Virol. 62, 875–881 (1988).

Gubler, U., and Hoffman, B. J., Gene 25, 263–269 (1983).

Guilhot, S., Hampe, A., D'Auriol, L., and Galibert, F. Virology 161, 252–258 (1987).

Guo, H.-G., diMarzo Veronese, F., Tschachler, E., Pal, R., Kalyanaraman, V. S., Gallo, R. C., and Reitz, Jr., M. S., Virology 174, 217–224 (1990).

Gupta, R. K., Misra, C. N., Gupta, V. K., and Saxena, S. N., Vaccine 9, 865–867 (1991).

Gurgo, C., Guo, H.-G., Franchini, G., Aldovini, A., Collalti, E., Farrell, K., Wong-Staal, F., Gallo, R. C., and Reitz, M. S., Jr., Virology 164, 531 (1988).

Haffar, O., Garrigues, J., Travis, B., Moran, P., Zarling, J. and Hu, S.-L., J. Virol. 64, 2653–2659, (1990).

Halpern, J. L., Habig, W. H., Neale, E. A., and Stibitz, S. *Infect. Immun.* 58, 1004–1009 (1990).

Hardy, Jr., W. D., Hess, P. W., MacEven, E. G., McClelland, A. J., Zuckerman, E. E., Essex, M., Cotter, S. M. and Jarrett, O., Cancer Res. 36 582–588 (1976).

Hardy, Jr., W. D., Adv. Viral Oncology 5, 1–34 (1985).

Hashimura, K., Kaminiyada, M., Akazaki, M., Yonemaru, K., Okuzono, Y., Hukomoto, M., Miura, Y., and Hayashi, S., J. Vet. Med. Sci. 34, 314–319 (in Japanese with English summary) (1981).

Hinshaw, V. S., Naeve, C. W., Webster, R. G., Douglas, A., Dkehel, J. J., and Bryans, J. T., Bull. World Health Orgaization 61, 153–158 (1983).

Hoshikawa, N., Kojima, A., Yasuda, A., Takayashiki, E., Masuko, S., Chiba, J., Sata, T., and Kurata, T., J. Gen, Virol. 72, 2509–2517 (1991).

Hosmalin, a., Nara, P. L., Zweig, M., Lerche, N. W., Cease, K. B., Gard, E. A., Markham, P. D., Putney, S. D., Daniel, M. D., Desrosiers, R. C., and Berzofsky, J. A. J. Immunol. 146, 1667–1673 (1991).

Hu, S.-L. Travis, B. M., Garrigues, J., Zarling, J. M. Sridhar, P., Dykers, T., Eichberg, J. W., and Alpers, C. Virology 179, 321–329 (1990).

Igarashi, A., J. Gen. Virol. 40, 531–544 (1978).

Inoue, Y. K., Bull. WHO 30, 181–185 (1964).

Ito, H., Maruyama, S., Yamashita, T., Tserumizu, T., Ogonuki, M., Matsui, S., Fuse, Y., Araki, H., Nishi, Y., Yamashita, M., Takabata, S., Sakurai, Y., and Otake, S., J. Vet. Med. Sci., 27, 331–334 (in Japanese with English summary) (1974).

Jahn, G., B-C. Scholl, B. Troupe, and B. Fleckenstein. J. Gen Virol. 68, 1327–1337 (1987).

Jarrett, O., and Russell, P. H., Int. J. Cancer 27, 466–472 (1978).

Jarrett, O., Hardy, Jr., W. D. Golder, M. C., and Hay, D., Int. J. Cancer 21, 334–337 (1978).

Jarrett, O., Laird, H. M., and Hay, D., J. Gen. Virol. 20, 169–175 (1973).

Jin, H. and Elliot, R. M., J. Virology 65, 4182–4189 (1991).

Joklik, W. K., Pickup, D. J., Patel, D. D., and Moody, M. D., Vaccine 6, 123–128 (1988).

Kari, B., N. Lussenhop, R. Goertz, M. Wabuke-Bunoti, R. Radeke, and R. Gehrz, J Virol. 60, 345–352 (1986).

Kawaoka, Y., Bean, W. J., Webster, R. G., Virology 169, 283–292 (1989).

Keegan, K. and Collett, M. S., J. Virology 58, 263–270 (1986).

Kensil, C. R., Barrett, M. S., Kushner, B. S., Beltz, G., Storey, J., Patel, U., Recchia, J., Aubert, A., and Marciaini, D., JAVMA 199, 1402–1405 (1991).

Kingsford, L., Ishizawa, L. D., and Hill, D. W., Virology 129, 443–455 (1983).

Kleitmann, W., Schottle, A., Kleitmann, B., et al., In Cell Culture Rabies Vaccines and Their Protective Effect in Man. ed. Kuwert/Wiktor/Koprowski, (International Green Cross–Geneva) pp. 330–337 (1981).

(List continued on next page.)

OTHER PUBLICATIONS

Knauf, V. C., and Nester, E. W., Plasmid 8, 45–54 (1982).

Kodama, K., Sasaki, N., and Kanda Inoue, Y., J. Immunol. 100, 194–200 (1967).

Konishi, E. Pincus, S., Fonseca, B. A. L., Shope, R. E., Paoletti, E., and Mason, P. W., Virology 185, 401–410 (1991).

Konno, J., Endo, K., Agatsuma, H., and Ishida, N. Cyclic, Am. J. Epidemiol. 84, 292–300 (1966).

Kurata, K., J. Vet. Med. Sci. 33, 85–87 (in Japanese) (1980).

Kuwert, E. K., Barsenbach, C., Werner, J., et al., In Cell Culture Rabies Vaccines and Their Protection Effect in Man, eds. Kuwert/Wiktor/Koprowski (International Green Cross–Geneva) pp. 160–167 (1981).

Leprevotte, I., Hampe, A., Sherr, C., and Galivert, F., J. Virol. 50, 884–894 (1984).

Liu, Y–N. C., A. Klaus, B. Kari, M. F. Stinski, J. Exhkardt, and R. C. Gehrz, J. Virol. 65, 1644–1648 (1991).

Lutz, H., Pedersen, N. C., and Higgens, J., Cancer Res. 40, 3642–3651 (1980).

Mackett, M., Smith, G. L., Moss, B., Proc. Natl. Acad. Sci. 79, 7415–7419 (1982).

Makoff, A. J., Ballantine, S. P., Smallwood, A. E., and Fairweather, N. F., *Bio/Technology* 7, 1043–1046 (1989).

Marshall, G. S., G. P. Rabalais, G. G. Stuart, and S. L. Waldeyer, J. Infect. Dis. 165, 381–384 (1992).

Mathes, L. E., Olsen, R. D., Hebebrand, L. C., Hoover, E. A., and Schaller, J. P., Nature 274, 687–691 (1978).

Mazzara, G. P., Destree, A. T., Williams, H. W., Sue. J. M., Belanger, L. M. and Panicali, D., Vaccines 87, 419–424 (1987).

Messing, J., vol. 101, eds, R. Wu, L. Grossman, and K. Moldave, (Academic Press, New York) pp. 20–78 (1983).

Mullins, J. I., and Hoover, E. A., In: Retrovirus Biology and Human Disease, (eds. Gallo, R. C., Wong-Staal, F.) Marcel Dekker, Inc., New York, pp. 87–116 (1990).

Nunberg, J. H., Williams, M. E., and Innis, M. A., J. Virol. 49, 629–632 (1984b).

Nunberg, J. H., Rodgers, J., Gilbert, J., and Snead, R. M., Proc. Natl. Acad. Sci. USA 81, 3675–3679 (1984a).

Ogasa, A., Yokoki, Y., Fujisaki, U., and Habu, A., Jpn. J. Anim. Reprod. 23, 171–175 (1977).

Oie, M., Shida, H., and Ichihashi, Y., Virology 176, 494–504 (1990).

Osterhaus, A., Wiejer, K., and UytdeHaag, F., Vaccine 7, 137–140 (1989).

Oya, A., Jpn. J. Med. Sci. Biol., Suppl., 20, 26–30 (1967).

Pachl, C., W. S. Probert, K. M. Hermsen, F. R. Masiarz, L. Rasmussen, T. C. Merigan, and R. R. Spaete, Virology 169, 418–426 (1989).

Pande, H., K. Campo, B. Tanamuchi, and J. A. Zaia, Virology 182, 220–228 (1991).

Panicali, D., Grezlecki, A., and Huang, C., gene 47, 193–199 (1986).

Parker, R. F., Bronson, L. H., and Green, R. H., J. Exp. Med. 74, 263–281 (1941).

Parrish, C. R., Aquadro, C. F., and Carmichael, L. E., Virology 166, 293–307 (1988).

Parrish, C. R., Aquadro, C. F., Strassheim, M. L., Evermann, J. F., Sgro, J–Y., and Mohammed, H. O., J. Virology 65, 6544–6552.

Parrish, C. R., Adv. Virus Res. 38, 403–450 (1990).

Pedersen, N. C., and Johnson, L., JAVMA 199, 1453–1455 (1991).

Pedersen, N. C., Johnson, L., and Oh, R. L., Feline Pract. 15, 7–20 (1985).

Plotkin, S. A., S. E. Starr, H. M. Friedman, E. Gonczol, and R. E. Weibel, J. Inf. Dis. 159, 860–865 (1989b).

Plotkin, S. A., H. M. Friedman, S. E. Starr, and E. Gonczol, In Contemporary Issues in Infectious Diseases, vol. 8, eds. Root et al. (Churchill Livingstone, New York) pp. 65–92 (1989a).

Pujisaki, Y., Sugimori, T., Morimoto, T., and Miura, U., Natl. Inst. Anim. Health Q. 15, 15–23 (1975a).

Rasmussen, L., M. Nelson, M. Neff, and T. C. Merigan, Jr., Virology 163, 308–318 (1988).

Reed, L. J. and Muench, H., Am. J. Hyg. 27, 493–497 (1938).

Research Committee for Prevention of Stillbirth in Sows due to Japanese Encephalitis. Prevention of stillbirth in sows by inoculation with killed Japanese encephalitis vaccine, Bull. Natl. Inst. Anim. Health 57, 1–8 (in Japanese with English summary) (1968).

Rickinson, A. B., Rowe, M., Hart, I. J., Yao, Q. Y., Henderson, L. E., Rabin, H., and Epstein, M. A., Cell. Immunol. 87, 646–658 (1984).

(List continued on next page.)

OTHER PUBLICATIONS

Rojko, J. L., and Olsen, R. G. (1984) Vet. Imm. Immunopath. 6, 107-165 (1984).

Rojko, J. L., Hoover, E. A., Quackenbush, S. L., and Osen, R. G., Nature 298, 385-388 (1982).

Romanos, M. A., Makoff, A. J., Fairweather, N. F., Beesley, K. M., Slater, D. E., Rayment, F. B., Payne, M. M., and Clare, J. J. Nucleic Acids Res. 19, 1461-1467 (1991).

Rooney, F. F., Wohlenberg, C., Cramer, E. J. et al., J. Virol. 62, 1530-1534 (1988).

Russell, P. H., and Jarrett, O., Int. J. Cancer 21, 768-778 (1978).

Russell, M., S. Kidd, and M. R. Kelley, Gene 45, 333-338 (1986).

Saliki, J. T., Mizak, B., Flore, H. P., Gettig, R. R., Burand, J. P., Carmichael, L. E., Wood, H. A., and Parrish, C. R., J. Gen. Virol. (accepted) (1992).

Sambrook, J., Fritsch, E. F., and Maniatis, T., In Molecular Cloning: A Laboratory Manual, 2nd Edition, (Cold Spring Harbor Laboratory, Cold Spring Harbor, N.Y.).

Sarma, P. S., and Log, T., Virology 54:160-169 (1973).

Sazawa, H., Sugimori, T., Morimoto, T., Miura, Y. and Watanabe, M., Natl. Inst. Anim. Health Q. 9, 74-82 (1969).

Scherer, W. F., Moyer, J. T., Izumi, T., Gresser, I., and McCown, J., Am. J. Trop. Med. Hyg. 8, 698-706 (1959).

Schmaljohn, C. S., Jennings, G. B., Hay, J., Dalrymple, J. M., Virology 155, 633-643 (1986).

Schmaljohn, C. S., and Dalrymple, J. M., Virology 131, 482-491 (1983).

Schmaljohn, C. S., Schmaljohn, A. L., and Dalrymple, J. M., Virology 157, 31-39 (1987).

Schmaljohn, C. S., Sugiyama, K., Schmaljohn, A. L., and Bishop, D. H. L., J. Gen. Virology 69, 777-786 (1988).

Schmaljohn, C. S., Chu, Y. K., Schmaljohn, A. L., and Dalrymple, J. M., J. Virology 64, 3162-3170 (1990).

Schmidt, D. M., Sidhu, N. K., Cianciolo, G. J., and Snyderman, R. (1987) Proc. Natl. Acad. Sci. USA 84, 7290-7294.

Sebring, R. W., Chu, H.-J., Chavez, L. G., Sandblom, D. S., Hustead, D. R., Dale, B., Wolf, D., Acree, W. M., (1991) JAVMA 199, 1413-1418.

Seligmann, E. B., In Laboratory Techniques in Rabies, eds. M. M. Kaplan and H. Koprowski, (World Health Organization, Geneva) pp. 279-285 (1973).

Shibley, G. P., Tanner, J. E., and Hanna, S. A., JAVMAK 199, 1402-1405 (1991).

Shimizu, T. and Kawakami, Y., Bull. Natl. Inst. Anim. Health, 23, 117-127 (1949).

Smith, J. S. and Yager, P. A. A rapid tissue culture test for determining rabies neutralization antibody. In: Laboratory Techniques on Rabies. Eds. M. M. Kaplan and H. Koprowski.

Sovinova, D., Tumova, B., Pouska, F., and Nemec, J., (1958).

Spehner, D., Gillard, S., Drillien, R., and Kirn, A., J. Virol. 62, 1297-1304 (1988).

Stewart, M. A., Warnock, M., Wheeler, A., Wiklie, N., Mullins, J. I., Oniono, D. E., and Neil, J. C. J. Virol. 58, 825-834 (1986).

Takahashi, M., JK. Med. Entomol. 13, 275-284 (1976).

Takehara, K., Mitsui, T., Nakamura, H., Fukusho, K., Kuramasu, S., and Nakamura, L., Nibs Bul. Biol. Res. 8, 23-37 (1969).

Tartaglia, J., M. E. Perkus, J. Taylor, E. K. Norton, J. C. Audonnet, W. I. Cox, S. W. Davis, J. VanderHoeven, B. Meignier, M. Riviere, B. Languet, and E. Paoletti, Virology 188 (1992).

Taylor, J., Weinberg, R., Tartaglia, J., Richardson, C., Alkhatib, G., Briedis, D., Appel, M., Norton, E., and Poaletti, E., Virology 187, 321-328 (1992).

Thomson, G. R., Spooner, P. R., and Powell, D. G., Vet. Res. 100, 465-468 (1977).

Tsubaki, S., Masu, S., Obata, Y., and Shimada, F., Kitasato Arch. Exp. Med., 23, 71-77 (1950).

Tsuchiya, N., Karaki, T., Kuroda, A., Karoji, Y., and Sasaki, O., Virus, 20, 290-300 (1970).

Turner, P. C. and Moyer, R. W., In Poxvirus, eds. R. W. Moyer and P. C. Turner, (Springer Verlag, N.Y.) pp. 125-152 (1990).

Varma, M. G., Pudney, M., and Leeke, C. J., Trans. R. Soc. Trop. Med. Hyg., 68, 374-382 (1974).

Waddell, G. H., Teigland, M. B., and Sigel, M. M., JAVMA 143, 587-590 (1963).

Watson, C. J., and Jackson, J. F., In: DNA Cloning, vol. I., ed., Glover, D. M., (IRL Press, Washington, D.C.), pp.79-88 (1985).

Waxham, M. N., Aronowski, J., Server, A. C., Wa- (List continued on next page.)

OTHER PUBLICATIONS linsky, J. S. Smith, J. A., and Goodman, H. M., Virology 164, 318–325 (1988).

Waxham, M. N., Server, A. C., Goodman, H. M., and Walinsky, J. S., Virology 159, 381–388 (1987).

Weibel, R. E., In: Vaccines, eds. Plotkin, S. A., and Mortimer, E. A., (W. B. Saunders), pp. 223–234 (1988).

Weston, K., and B. G. Barrell, J. Mol. Biol. 192, 177–208 (1986).

WHO Meeting, Geneva, Jun. 19–22, Vaccine 8, 425–437 (1990).

Wolff, L. H., Mathes, L. E., and Osone, R. G., J. Immunol. Meth. 26, 151–156 (1979).

Wolinsky, J. S., and Waxham, M. N., In: Virology, eds. Fields, B. N., and Knipe, D. M., (Raven Press), pp. 989–1011 (1990).

Wunsch, M., Schultz, A. S., Koch, W., Friedrich, R., and Hunsmann, G., EMBO J. 2, 2239–2246 (1983).

Yamagishi, A., J. Vet. Med. 820, 14–18 (1989).

Yamanishi, K., Dantas, J. R., Jr., Takahashi, M., Yamanouchi, T., Damae, K., Takahoashi, Y., Tanishita, O., J. Virology 52, 231–237 (1984).

Yasuda, A., Kimura-Kuroda, J. Ogimoto, M., Miyamoto, M., Sata, T., Sato, T., Takamura, C., Kurata, T., Kojima, A., and Yasui, K., J. Virol. 64, 2788–2795 (1990).

Yoshida, I., Takagi, M., Inokuma, E., Goda, H., Ono, K., Takaku, K., and Oku, J., Biken J. 24, 47–67 (1981).

Yoshinaka, Y., Katch, I., Copeland, T. D. and Oroszlan, S., J. Virol. 55, 870–873 (1985).

Zhang, X.-K., Takashima, I., and Hashimoto, N., Arch. Virol., 105, 235–246 (1989).

Zingernagel, R. M., Sato, T., Althage, A., and Kamisaku, H., Eur. J. Immunol. 14, 14–23 (1984).

Lai et al., "Attenuated Deletion Mutants of Vaccinia Virus Lacking the Vaccinia Growth Factor are Defective in Replication in vivo," *Microbial Pathogenesis*, vol. 6, No. 3, pp. 219–226 (1989).

Beck, E., Ludwig, G., Auerswald, E. A., Reiss, B., and H. Schaller, Gene 19, 327–336 (1982).

Boyle, D. B., and B. E. H. Coupar, Gene 65, 123–128 (1988).

Drillien, R., Spehner, D., and A. Kirn, J. Virol. 28, 843–850 (1978).

Falkner, F. G. and B. Moss, J. Virol. 62, 1849–1854 (1988).

Fathi, Z., Sridhar, P., Pacha, R. F., and R. C. Condit, Virology 155, 97–105 (1986).

Fenner, F. and J. F. Sambrook, Virology 28, 600–609 (1966).

Franke, C. A., Rice, C. M., Strauss, J. H., and D. E. Hruby, Mol. Cell. Biol. 5, 1918–1924 (1985).

Gangemi, J. D. and D. G. Sharp, Virology 85, 262–270 (1978).

Gemmell, A. and F. Fenner, Virology 11, 219–235 (1960).

Gillard, S., Spehner, D., and R. Drillien, J. Virol. 53, 316–318 (1985).

Graham, F. L. and A. J. Van der Eb, Virology 54, 536–539 (1973).

Hruby, D. E., Lynn, D. L., Condit, R., and J. R. Kates, J. gen Virol. 47, 485–488 (1980).

Lake, J. R. and P. D. Cooper, J. gen Virol. 48, 135–147 (1980).

Mackett, M., Smith, G. L. and B. Moss, Proc. Natl. Acad. Sci. USA 79, 7415–7419 (1982).

Mayr, A., Hochstein-Mintzel, V., and H. Stickl, Infection 3, 6–14 (1975).

McClain, M. E., Aust. J. exp. Biol. med. Sci. 43, 31–44 (1965).

Moyer, R. W. and C. T. Rothe, Virology 102, 119–132 (1980).

Nakano, E., Panicali, D., and E. Paoletti, Proc. Natl. Acad. Sci. USA 79, 1593–1596 (1982).

Rosel, J. L., Earl, P. L., Weir, J. P., and B. Moss, J. Virol. 60 436–449 (1986).

Southern, P. H. and P. Berg, J. Mol. Appl. Genet. 1, 327–341 (1982).

Tagaya, I., Kitamura, T., and Y. Sano, Nature (London) 192, 381–382 (1961).

Wilson, E. M., Hodges, W. M., and D. E. Hruby, Gene 49, 207–213 (1986).

Southern, E. M., J. Mol. Biol. 98, 503–517 (1975).

Tamin, A., Villarreal, E. C., Weinrich, S. L., and D. E. Hruby, Virology 165, 141–150 (1988).

Kaplan, J. M., Mardon, G., Bishop, J. M., and H. E. Varmus, Mol. Cell. Biol. 8, 2435–2441 (1988).

Baroudy, B. M., Venkatesan, S., and B. Moss, Cell 28, 315–324 (1982).

Wittek, R. and B. Moss, Cell 21, 277–284 (1980).

Wittek, R., Muller, H. K., Menna, A., and R. Wyler, (List continued on next page.)

OTHER PUBLICATIONS

FEBS Letters 90, 41–46 (1978).
Isle et al., Virology 112, 306–317 (1981).
Altenburger, W., C-P. Suter and J. Altenburger, Archives Virol. 105, 15–27 (1989).
Behbehani, A. M., Microbiological Reviews 47, 455–509 (1983).
Bergoin, M. and S. Dales, In *Comparative Virology*, pp. 169–205 (edited by K. Maramorosch and E. Kurstak, Academic Press, New York) (1971).
Bertholet, C., R. Drillien and R. Wittek, Proc. Natl. Acad. Sci. 82, 2096–2100 (1985).
Buller, R. M. L., G. L. Smith, K. Cremer, Nature 317, 813–815 (1985).
Child, S. J., G. J. Palumbo, R. M. L. Buller and D. E. Hruby, Virology 174, 625–629 (1990).
Clewell, D. B., J. Bacteriol 110, 667–676 (1972).
Clewell, D. B. and D. R. Helinski, Proc. Natl. Acad. Sci. USA 62, 1159–1166 (1969).
Colinas, R. J., R. C. Condit and E. Paoletti, Virus Research 18, 49–70 (1990).
Drillien, R., F. Koehren and A. Kirn, Virology 111, 488–499 (1981).
Engelke, D. R., P. A. Hoener and F. S. Collins, Proc. Natl. Acad. Sci. USA 85, 544–548 (1988).
Funahashi, S., T. Sato and H. Shida, J. Gen. Virol. 69, 35–47 (1988).
Gillard, S., D. Spehner, R. Drillien and A. Kirn, Proc. Natl. Acad. Sci. USA 83, 5573–5577 (1986).
Goebel, S. J., Johnson, G. P., Perkus, M. E., Davis, S. W., Winslow, J. P. and E. Paoletti, Virology 179, 247–266 (1990).
Goebel, S. J., G. P. Johnson, M. E. Perkus, S. W. Davis, J. P. Winslow and E. Paoletti, Virology 179, 517–563 (1990).
Goldstein, D. J. and S. K. Weller, Virology 166, 41–51 (1988).
Guo, P., S. Goebel, S. Davis, M. E. Perkus, B. Languet, P. Desmettre, G. Allen and E. Paoletti, J. Virol. 63, 4189–4198 (1989).
Guo, P., S. Goebel, M. E. Perkus, J. Taylor, E. Norton, G. Allen, B. Languet, P. Desmettre and E. Paoletti, J. Virol. 64, 2399–2406 (1990).
Hruby, D. E. and L. A. Ball, J. Virol. 43, 403–409 (1982).
Hruby, D. E., R. A. Maki, D. B. Miller and L. A. Ball, Proc. Natl. Acad. Sci. USA 80, 3411–3415 (1983).
Ichihashi, Y. and Dales, S., Virology 46, 533–543 (1971).
Itamura, S., H. Iinuma, H. Shida, Y. Morikawa, K. Nerome and A. Oya, J. Gen. Virol. 71, 2859–2865 (1990).
Jacobson, J. G., D. A. Leib, D. J. Goldstein, C. L. Bogard, P. A. Schaffer, S. K. Weller and D. M. Coen, Virology 173, 276–283 (1989).
Jamieson, A. T., G. A. Gentry and J. H. Subak-Sharpe, J. Gen. Virol. 24, 465–480 (1974).
Kato, S., M. Takahashi, S. Kameyama and J. Kamahora, Biken's 2, 353–363 (1959).
Kotwal, G. J., A. W. Hugin and B. Moss, Virology 171, 579–587 (1989).
Kotwal, G. J., S. N. Isaacs, R. McKenzie, M. M. Frank and B. Moss, Science 250, 827–830 (1990).
Kotwal, G. J. and B. Moss, Nature 335, 176–178 (1988a).
Kotwal, G. J. and B. Moss, Virology 167, 524–537 (1988b).
Kotwal, G. J. and B. Moss, J. Virol. 63, 600–606 (1989).
Lai, A. C.-K. and B. G.-T. Pogo, Virus Res. 12, 239–250 (1989).
Mandecki, W., Proc. Natl. Acad. Sci. USA 83, 7177–7181 (1986).
Maniatis, T., E. F. Fritsch and J. Sambrook, Cold Spring Harbor Laboratory, Cold Spring Harbor, N.Y. (1982).
Morgan, A. J., M. Mackett, S. Finerty, J. R. Arand, F. T. Scullion and M. A. Epstein, J. Med. Virol. 25, 189–195 (1988).
Moss, B., E. Winters and J. A. Cooper, J. Virol. 40, 387–395 (1981).
Paez, E., S. Dallo and M. Esteban, Proc. Natl. Acad. Sci. USA 82, 3365–3369 (1985).
Palumbo, G. J., D. J. Pickup, T. N. Fredrickson, L. J. McIntyre and R. M. L. Buller, Virology 172, 262–273 (1989).
Panicali, D., S. W. Davis, S. R. Mercer and E. Paoletti, J. Virol. 37, 1000–1010 (1981).
Panicali, D. and E. Paoletti, Proc. Natl. Acad. Sci. USA 79, 4927–4931 (1982).
Patel, D. D. and D. J. Pickup, EMBO 6, 3787–3994 (1987).
Patel, D. D., C. A. Ray, R. P. Drucker, D. J. Pickup, Proc. Natl. Acad. Sci. USA 85, 9431–9435 (1988).

(List continued on next page.)

OTHER PUBLICATIONS

Perkus, M. E., S. J. Goebel, S. W. Davis, G. P. Johnson, K. Limbach, E. K. Norton and E. Paoletti, Virology 179, 276–286 (1990).

Perkus, M. E., S. J. Goebel, S. W. Davis, G. P. Johnson, E. K. Norton and E. Paoletti, Virology 180, 406–410 (1991).

Perkus, M. E., K. Limbach and E. Paoletti, J. Virol. 63, 3829–3836 (1989).

Perkus, M. E., D. Panicali, S. Mercer and E. Paoletti, Virology 152, 285–297 (1986).

Perkus, M. E., A. Piccini, B. R. Lipinskas and E. Paoletti, Science 229, 981–984 (1985).

Piccini, A., M. E. Perkus and E. Paoletti, Methods Enzymol. 153, 545–563 (1987).

Pickup, D. J., B. S. Ink, W. Hu, C. A. Ray and W. K. Joklik, Proc. Natl. Acad. Sci. USA 83, 7698–7702 (1986).

Pickup, D. J., B. S. Ink, B. L. Parsons, W. Hu and W. K. Joklik, Proc. Natl. Acad. Sci. USA 81, 6817–6821 (1984).

Sanger, F., S. Nicklen and A. R. Coulson, Proc. Natl. Acad. Sci. USA 74, 5463–5467 (1977).

Schmitt, J. F. C. and H. G. Stunnenberg, J. Virol. 62, 1889–1897 (1988).

Shapira, S. K., Chou, J., Richaud, F. V. and Casadaban, M. J., Gene 25, 71–82 (1983).

Shida, H., Virology 150, 451–462 (1986).

Shida, H., Y. Hinuma, M. Hatanaka, M. Morita, M. Kidokoro, K. Suzuki, T. Maruyama, F. Takahashi-Nishimaki, M. Sugimoto, R. Kitamura, T. Miyazawa and M. Hayami, J. Virol. 62, 4474–4480 (1988).

Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).

Slabaugh, M., N. Roseman, R. Davis and C. Mathews, J. Virol. 62, 519–527 (1988).

Stanberry, L. R., S. Kit and M. G. Myers, J. Virol. 55, 322–328 (1985).

Tabor, S. and C. C. Richardson, Proc. Natl. Acad. Sci. USA 84, 4767–4771 (1987).

Tartaglia, J., S. Pincus and E. Paoletti, Critical Reviews in Immunology 10, 13–30 (1990).

Taylor, G., E. J. Stott, G. Wertz and A. Ball, J. Gen. Virol. 72, 125–130 (1991).

Taylor, J., R. Weinberg, L. Kawaoka, R. G. Webster and E. Paoletti, Vaccine 6, 504–506 (1988).

Taylor, J., R. Weinberg, B. Lanquet, P. Desmettre, and E. Paoletti, Vaccine 6, 497–504 (1988).

Weir, J. P. and B. Moss, J. Virol. 46, 530–537 (1983).

Zhou, J., L. Crawford, L. McLean, X. Sun, M. Stanley, N. Almond and G. L. Smith, J. Gen. Virol. 71, 2185–2190 (1990).

Tartaglia et al. (1992) Virology 188:217–32.

Moon Soo Lee et al. (1992) J. Virol 66(5):2617–30.

Edbauer, C., R. Weinberg, J. Taylor, A. Rey-Senelonge, J. F. Bouquet, P. Desmettre, and E. Paoletti, Virology 179, 901–904 (1990).

Hu, S.-L., Fultz, P., McClure, H., Eichberg, J., Thomas, E., Zarling, J., Singhal, M., Kosowski S., Swenson, R., Anderson, D. and Todaro, G., Nature 328, 721–723 (1987).

Easterday, B. C. and V. S. Hinshaw, In Diseases of Poultry, Ninth edition, eds. B. W. Calnek, H. J. Barnes, et al., (Iowa State University Press, Ames, Iowa) pp. 531–551 (1991).

FIG. I

GENETICALLY ENGINEERED VACCINE STRAIN

This application is a continuation division of application Ser. No. 07/666,056, filed Mar. 7, 1991 now abandoned.

FIELD OF THE INVENTION

The present invention relates to a modified poxvirus and to methods of making and using the same. More in particular, the invention relates to an improved vector for the insertion and expression of foreign genes for use as safe immunization vehicles to protect against a variety of pathogens.

Several publications are referenced in this application by arabic numerals within parentheses. Full citation to these references is found at the end of the specification immediately preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (47).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (7) and isolated (8,33).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are postvaccinial encephalitis and generalized vaccinia (2).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in 59).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (34).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (19) and sequenced (20,63). Inactivation or complete deletion of the thymidine kinase gene does not prevent growth of vaccinia virus in a wide variety of cells in tissue culture. TK⁻ vaccinia virus is also capable of replication in vivo at the site of inoculation in a variety of hosts by a variety of routes.

It has been shown for herpes simplex virus type 2 that intravaginal inoculation of guinea pigs with TK− virus resulted in significantly lower virus titers in the spinal cord than did inoculation with TK+ virus (57). It has been demonstrated that herpesvirus encoded TK activity in vitro was not important for virus growth in actively metabolizing cells, but was required for virus growth in quiescent cells (24).

Attenuation of TK− vaccinia has been shown in mice inoculated by the intracerebral and intraperitoneal routes (5). Attenuation was observed both for the WR neurovirulent laboratory strain and for the Wyeth vaccine strain. In mice inoculated by the intradermal route, TK− recombinant vaccinia generated equivalent antivaccinia neutralizing antibodies as compared with the parental TK+ vaccinia virus, indicating that in this test system the loss of TK function does not significantly decrease immunogenicity of the vaccinia virus vector. Following intranasal inoculation of mice with TK− and TK+ recombinant vaccinia virus (WR strain), significantly less dissemination of virus to other locations, including the brain, has been found (60).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (16). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (23).

Both the small (56) and large (51) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (6).

The vaccinia virus hemagglutinin gene (HA) has been mapped and sequenced (53). The HA gene of vaccinia virus is nonessential for growth in tissue culture (21). Inactivation of the HA gene of vaccinia virus results in reduced neurovirulence in rabbits inoculated by the intracranial route and smaller lesions in rabbits at the site of intradermal inoculation (54). The HA locus was used for the insertion of foreign genes in the WR strain (55), derivatives of the Lister strain (54) and the Copenhagen strain (17) of vaccinia virus. Recombinant HA− vaccinia virus expressing foreign genes have been shown to be immunogenic (17,22,54,55) and protective against challenge by the relevant pathogen (17,55).

Cowpox virus (Brighton red strain) produces red (hemorrhagic) pocks on the chorioallantoic membrane of chicken eggs. Spontaneous deletions within the cowpox genome generate mutants which produce white pocks (49). The hemorrhagic function (u) maps to a 38 kDa protein encoded by an early gene (48). This gene, which has homology to serine protease inhibitors, has been shown to inhibit the host inflammatory response to cowpox virus (37) and is an inhibitor of blood coagulation.

The u gene is present in WR strain of vaccinia virus (30). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (64). The u region is present in a defective nonfunctional form in Copenhagen strain of vaccinia virus (open reading frames B13 and B14 by the terminology reported in references 14 and 15).

Cowpox virus is localized in infected cells in cytoplasmic A type inclusion bodies (ATI) (25). The function of ATI is thought to be the protection of cowpox virus virions during dissemination from animal to animal (3). The ATI region of the cowpox genome encodes a 160 kDa protein which forms the matrix of the ATI bodies (12,40). Vaccinia virus, though containing a homologous region in its genome, generally does not produce ATI. In WR strain of vaccinia, the ATI region of the genome is translated as a 94 kDa protein (41). In Copenhagen strain of vaccinia virus, most of the DNA sequences corresponding to the ATI region are deleted, with the remaining 3′ end of the region fused with sequences upstream from the ATI region to form open reading frame (ORF) A26L (14,15).

A variety of spontaneous (1,10,31,35,36,38) and engineered (43-45) deletions have been reported near the left end of the vaccinia virus genome. A 10 kb spontaneous deletion in WR strain of vaccinia virus (35,38) was shown to be attenuated by intracranial inoculation in mice (5). This deletion was later shown to include 17 potential ORFs (29). Specific genes within the deleted region include the virokine N1L and a 35 kDa protein (C3L, by the terminology reported in references 14 and 15). Insertional inactivation of N1L reduces virulence by intracranial inoculation for both normal and nude mice (26). The 35 kDa protein is secreted like N1L into the medium of vaccinia virus infected cells. The protein contains homology to the family of complement control proteins, particularly the complement 4B binding protein (C4bp) (28). Like the cellular C4bp, the vaccinia 35 kDa protein binds the fourth component of the complement and inhibits the classical complement cascade (27). Thus the vaccinia 35 kDa protein appears to be involved in aiding the virus in evading host defense mechanisms.

The left end of the vaccinia genome includes two genes which have been identified as host range genes, K1L (13) and C7L (42). Deletion of both of these genes reduces the ability of vaccinia virus to grow on a variety of human cell lines (42).

It can be appreciated that provision of a novel vaccine strain having enhanced safety would be a highly desirable advance over the current state of technology.

OBJECTS OF THE INVENTION

It is therefore an object of this invention to provide modified recombinant viruses, which viruses have enhanced safety, and to provide a method of making such recombinant viruses.

It is an additional object of this invention to provide a recombinant poxvirus vaccine having an increased level of safety compared to known recombinant poxvirus vaccines.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety.

These and other objects and advantages of the present invention will become more readily apparent after consideration of the following.

STATEMENT OF THE INVENTION

In one aspect, the present invention relates to a modified recombinant virus having inactivated nonessential virus-encoded encoded genetic functions so that the recombinant poxvirus has attenuated virulence and enhanced safety. The virus is advantageously a poxvirus, particularly a vaccinia virus.

In another aspect, the present invention relates to a vaccine for inducing an immunological response in a host animal inoculated with the vaccine, said vaccine including a carrier and a modified recombinant virus having inactivated nonessential virus-encoded genetic functions so that the recombinant poxvirus has attenuated virulence and enhanced safety. The virus used in the vaccine according to the present invention is advantageously a poxvirus, particularly a vaccinia virus.

In yet another aspect, the present invention relates to a method for expressing a gene product in a cell cultured in vitro by introducing into the cell a modified recombinant virus having attenuated virulence and enhanced safety.

In a still further aspect, the present invention relates to a modified recombinant vaccinia virus having nonessential virus-encoded genetic functions inactivated therein so that the virus has attenuated virulence, and wherein the modified recombinant vaccinia virus further contains DNA from a non-vaccinia source in a nonessential region of the vaccinia genome. In particular, the genetic functions are inactivated by deleting an open reading frame encoding a virulence factor or by insertional inactivation of an open reading frame encoding a virulence factor. Advantageously, the open reading frame is selected from the group consisting of J2R, B13R+B14R, A26L, A56R, C7L - K1L, and I4L (by the terminology reported in references 14 and 15). In this respect, the open reading frame comprises a thymidine kinase gene, a hemorrhagic region, an A type inclusion body region, a hemagglutinin gene, a host range gene region or a large subunit, ribonucleotide reductase.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION OF THE INVENTION

Figure 1:
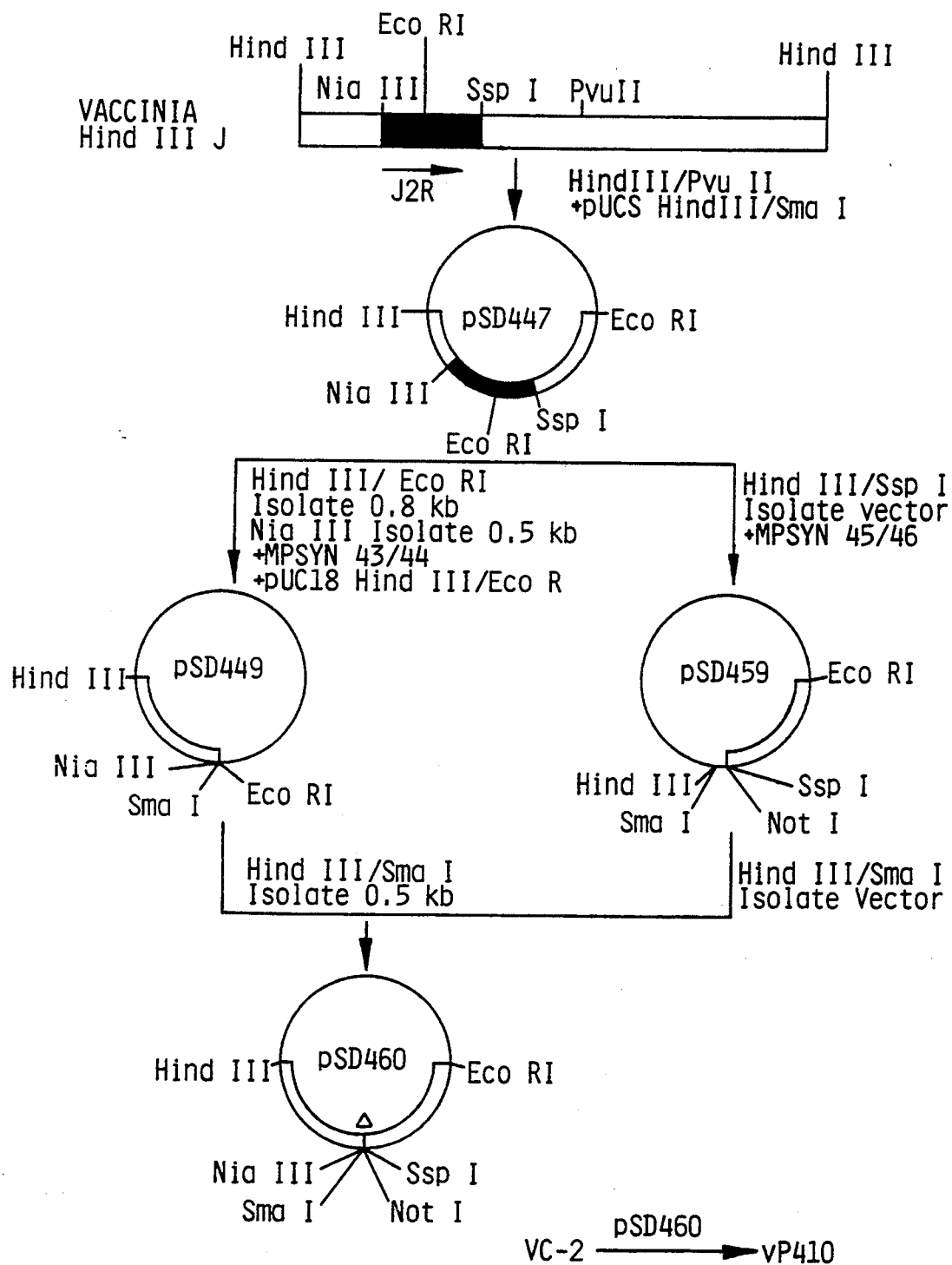
FIG. 1 schematically shows a method for the construction of plasmid pSD460 for deletion of thymidine kinase gene and generation of recombinant vaccinia virus vP410.

To develop the new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in references 14 and 15.

The deletion loci were also engineered as recipient loci for the insertion of foreign genes.

The regions sequentially deleted in NYVAC are listed below. Also listed are the abbreviations and open reading frame designations for the deleted regions (14,15) and the designation of the vaccinia recombinant (vP) containing all deletions through the deletion specified:

(1) thymidine kinase gene (TK; J2R) vP410;
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L - K1L) vP804; and
(6) large subunit, ribonucleotide reductase (I4L) vP866 (NYVAC).

DNA Cloning and Synthesis. Plasmids were constructed, screened and grown by standard procedures (33,46,47) . Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (44). DNA sequencing was performed by the dideoxy-chain termination method (50) using Sequenase (58) as previously described (17). DNA amplification by polymerase chain reaction (PCR) for sequence verification (11) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (32) using synthetic oligonucleotides.

Cells, Virus, and Transfection. The origins and conditions of cultivation of the Copenhagen strain of vaccinia virus has been previously described (17). Generation of recombinant virus by recombination, in situ hybridization of nitrocellulose filters and screening for B-galactosidase activity are as previously described (39,44).

A better understanding of the present invention and of its many advantages will be had from the following examples, given by way of illustration.

EXAMPLE 1

CONSTRUCTION OF PLASMID pSD460 FOR DELETION OF THYMIDINE KINASE GENE (J2R)

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44

were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46

generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wildtype parental vaccinia virus Copenhagen strain VC-2. $^{32}$P labelled probe was synthesized by primer extension using MPSYN45 as template and the complementary 20mer oligonucleotide MPSYN47 (5′ TTAGTTAATTAGGCGGCCGC 3′) as primer. Recombinant virus vP410 was identified by plaque hybridization.

EXAMPLE 2

CONSTRUCTION OF PLASMID pSD486 FOR DELETION OF HEMORRHAGIC REGION (B13R+B14R)

Figure 2:
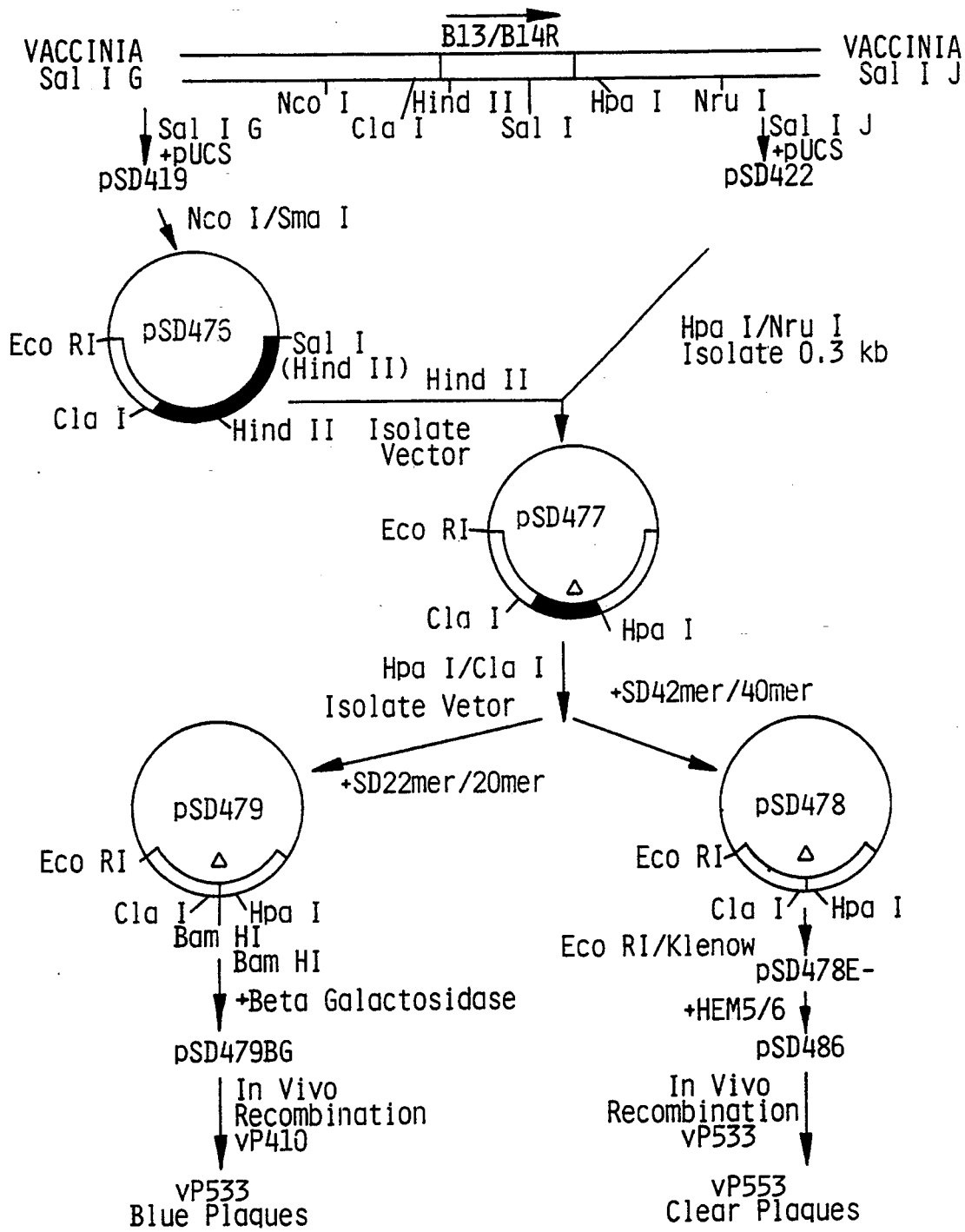
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R - B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer

generating pSD479. pSD479 contains an initiation codon (underlined) followed by a BamHI site. To place E. coli Betagalactosidase in the B13-B14 (u) deletion locus under the control of the u promoter, a 3.2 kb BamHI fragment containing the Betagalactosidase gene (52) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R-B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer

```
         ClaI               SacI            XhoI              HpaI
SD42mer 5' CGATTACTAGATCTGAGCTCCCCGGGCTCGAGGGATCCGTT 3'
SD40mer 3'    TAATGATCTAGACTCGAGGGGCCCGAGCTCCCTAGGCAA 5'
            BglII              SmaI             BamHI
``` generating plasmid pSD478. Next the EcoRI site at the pUC/vaccinia junction was destroyed by digestion of pSD478 with EcoRI followed by blunt ending with Klenow fragment of *E. coli* polymerase and ligation, generating plasmid pSD478E⁻. pSD478E⁻ was digested with BamHI and HpaI and ligated with annealed synthetic oligonucleotides HEM5/HEM6

```
         BamHI    EcoRI    HpaI
HEM5  5' GATCCGAATTCTAGCT 3'
HEM6  3'     GCTTAAGATCGA 5'
``` generating plasmid pSD486. pSD486 was used as donor plasmid for recombination with recombinant vaccinia virus vP533, generating vP553, which was isolated as a clear plaque in the presence of X-gal.

EXAMPLE 3

CONSTRUCTION OF PLASMID pMP494Δ FOR DELETION OF ATI REGION (A26L)

Figure 3:
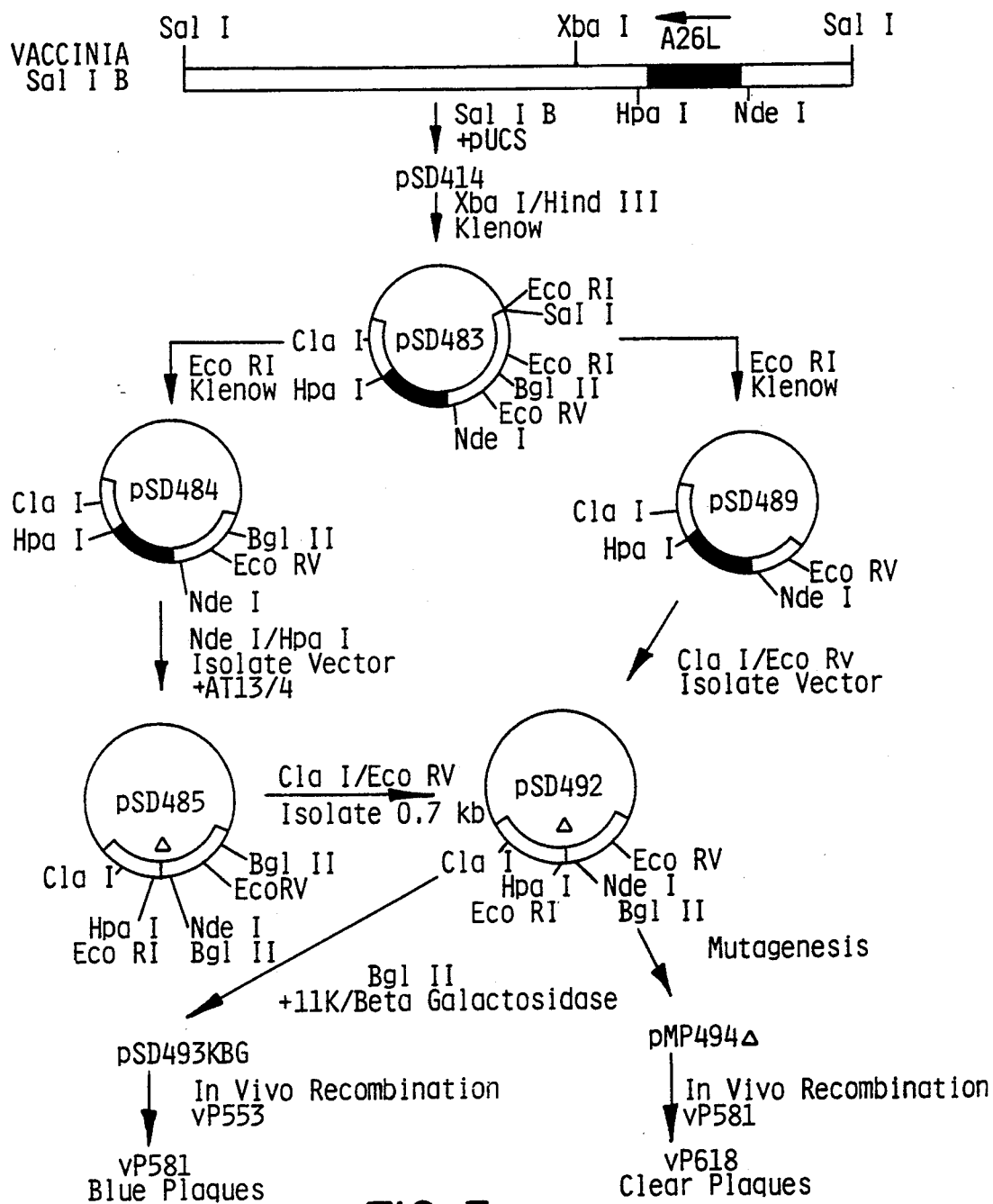
FIG. 3 schematically shows a method for the construction of plasmid pMP494Δ a for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of *E. coli* polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BglII cassette containing the *E. coli* Betagalactosidase gene (52) under the control of the vaccinia 11 kDa promoter (4,42) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Betagalactosidase sequences from vaccinia recombinant virus vP581, the polylinker region of plasmid pSD492 was deleted by mutagenesis (32) using synthetic oligonucleotide MPSYN177 (5' AAAATGGGCGTGGATTGT-TAACTTTATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

EXAMPLE 4

CONSTRUCTION OF PLASMID pSD467 FOR DELETION OF HEMAGGLUTININ GENE (A56R)

Figure 4:
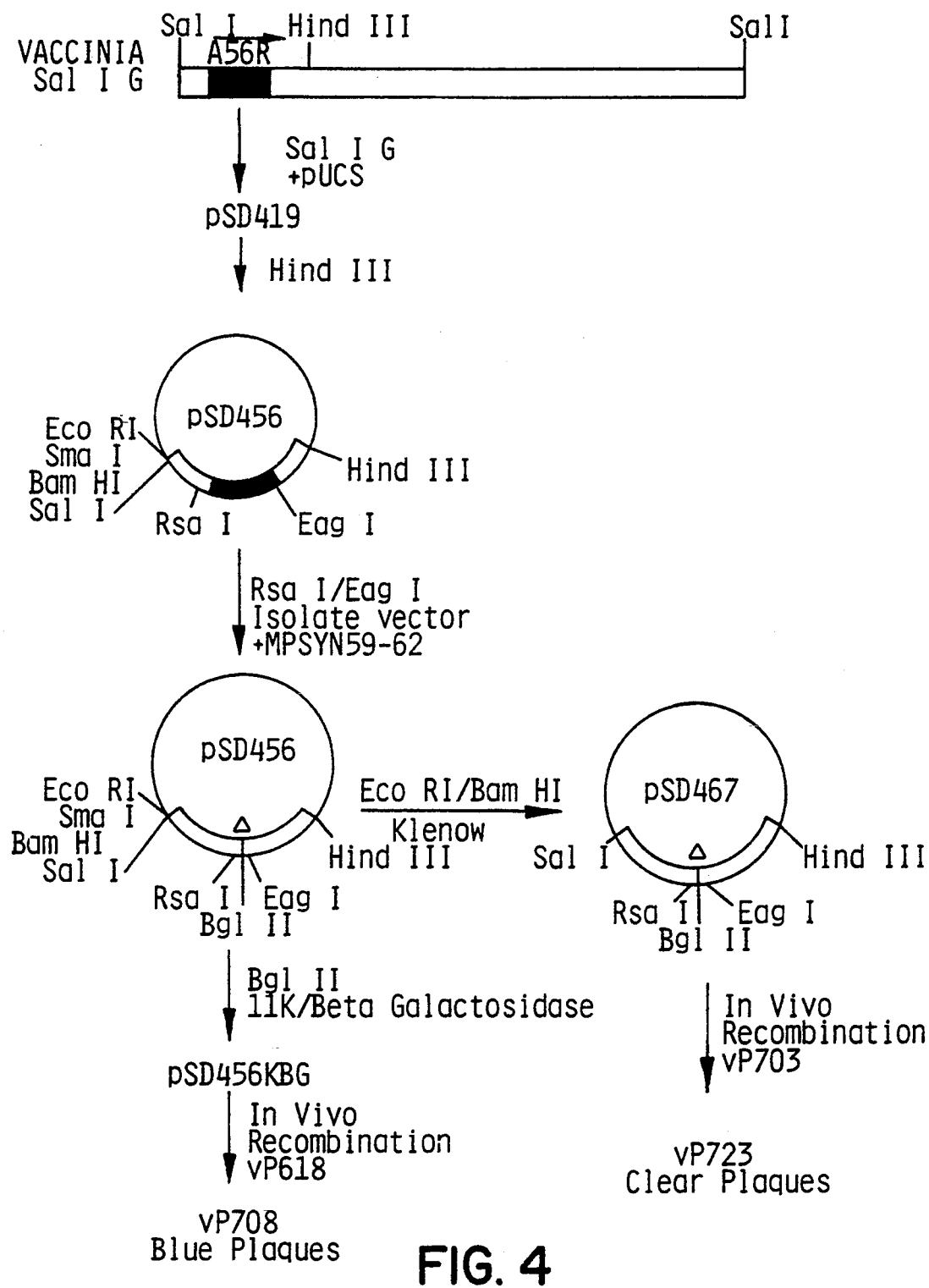
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from Hin-

```
      NdeI
ATI3 5' TATGAGTAACTTAACTCTTTTGTTAATTAAAAGTATATTCAAAAAATAAGT
ATI4 3'    ACTCATTGAATTGAGAAAACAATTAATTTTCATATAAGTTTTTATTCA
```

```
         BglII    EcoRI    HpaI
       TATATAAATAGATCTGAATTCGTT   3' ATI3
       ATATATTTATCTAGACTTAAGCAA   5' ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of *E. coli* polymerase and ligation. The resulting plasmid was designated pSD489. The 1.8 kb ClaI (pos. 137,198)/EcoRV (pos. 139,048) fragment from pSD489 dIII B were removed by digestion of pSD419 with HindIII within vaccinia sequences and at the pUC/vaccinia junction followed by ligation. The resulting plasmid, pSD456, contains the HA gens, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gens. The 3.6 kb RsaI/EagI vector fragment from pSD456 was isolated and ligated with annealed synthetic oligonucleotides MPSYN59-62

```
              RsaI
MPSYN49 5'  ACACGAATGATTTTCTAAAGTATTTGGAAAGTTTTATAGGTAGTTGATAGA—
MPSYN62 3'  TGTGCTTACTAAAAGATTTCATAAACCTTTCAAAATATCCATCAACTATCT  5'
```

MPSYN59   —ACAAAATACATAATTT   3'

BglII

MPSYN60   5'                                      TGTAAAAATAAATCACTTTTTATACTAAGATCT—
MPSYN61   3'   TGTTTTATGTATTAAAACATTTTTATTTAGTGAAAAATATGATTCTAGA—

SmaI    PstI    EagI
MPSYN60   —CCCGGGCTGCAGC               3'
MPSYN61   —GGGCCCGACGTCGCCGG   5' reconstructing the DNA sequences upstream from the A56R ORF and replacing the A56R ORF with a polylinker region as indicated above. The resulting plasmid is pSD466. The vaccinia deletion in pSD466 encompasses positions [161,185–162,053]. The site of the deletion in pSD466 is indicated by a triangle in FIG. 4.

A 3.2 kb BglII/BamHI (partial) cassette containing the *E. coli* Beta-galactosidase gene (52) under the control of the vaccinia 11 kDa promoter (4,17) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of *E. coli* polymerase and ligation. Recombination between vP708 and pSD467 resulted in recombinant vaccinia deletion mutant, vP723, which was isolated as a clear plaque in the presence of X-gal.

EXAMPLE 5

CONSTRUCTION OF PLASMID pMPCSKIΔ FOR DELETION OF OPEN READING FRAMES [C7L-K1L]

Figure 5:
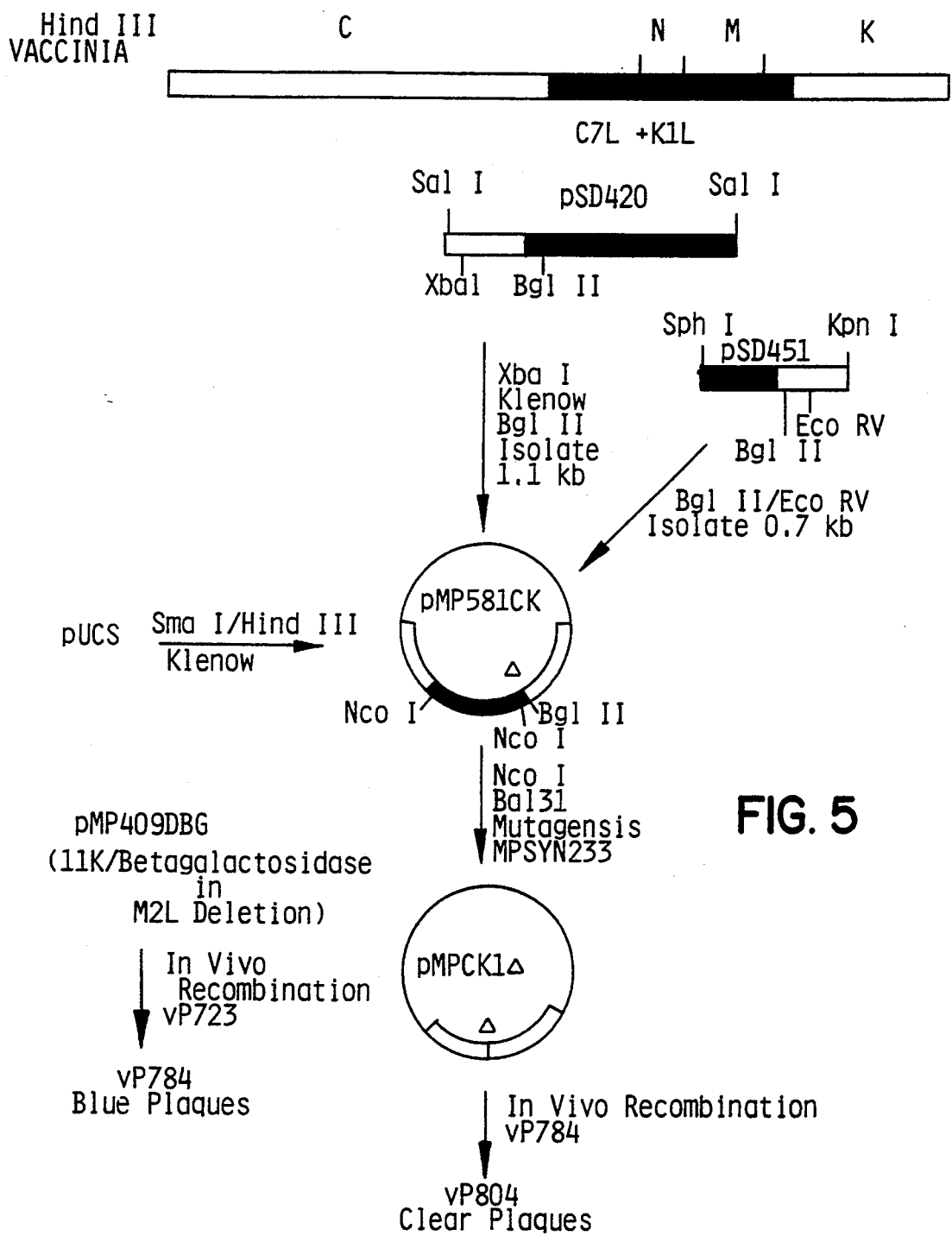
FIG. 5 schematically shows a method for the construction of plasmid pMPCSK1Δ for deletion of gene cluster [C7L - K1L] and generation of recombinant vaccinia virus vP804.

Referring now to FIG. 5, the following vaccinia clones were utilized in the construction of pMPCSKIΔ. pSD420 is SalI H cloned into pUCS. pSD435 is KpnI F cloned into pUC18. pSD435 was cut with SphI and religated, forming pSD451. In pSD451, DNA sequences to the left of the SphI site (pos. 27,416) in HindIII M are removed (42). pSD409 is HindIII M cloned into pUC8.

To provide a substrate for the deletion of the [C7LK1L] gene cluster from vaccinia, *E. coli* Beta-galactosidase was first inserted into the vaccinia M2L deletion locus (18) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (18,32) using synthetic oligonucleotide pMP409D cut with BglII. The resulting plasmid, pMP409DBG (18), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L-K1L] was assembled in pUC8 cut with SmaI, HindIII and blunt ended with Klenow fragment of *E. Coli* polymerase. The left flanking arm consisting of vaccinia HindIII C sequences was obtained by digestion of pSD420 with XbaI (pos. 18,628) followed by blunt ending with Klenow fragment of *E. Coli* polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (32) using synthetic oligonucleotide MPSYN233 5' TGTCATTTAACACTATACTCATAT-TAATAAAAATAATATTTATT 3'. The resulting plasmid, pMPCSK1Δ, is deleted for vaccinia sequences positions 18,805–29,108, encompassing 12 vaccinia open reading frames [C7L - K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

EXAMPLE 6

CONSTRUCTION OF PLASMID pSD548 FOR DELETION OF LARGE SUBUNIT, RIBONUCLEOTIDE REDUCTASE (I4L)

Figure 6:
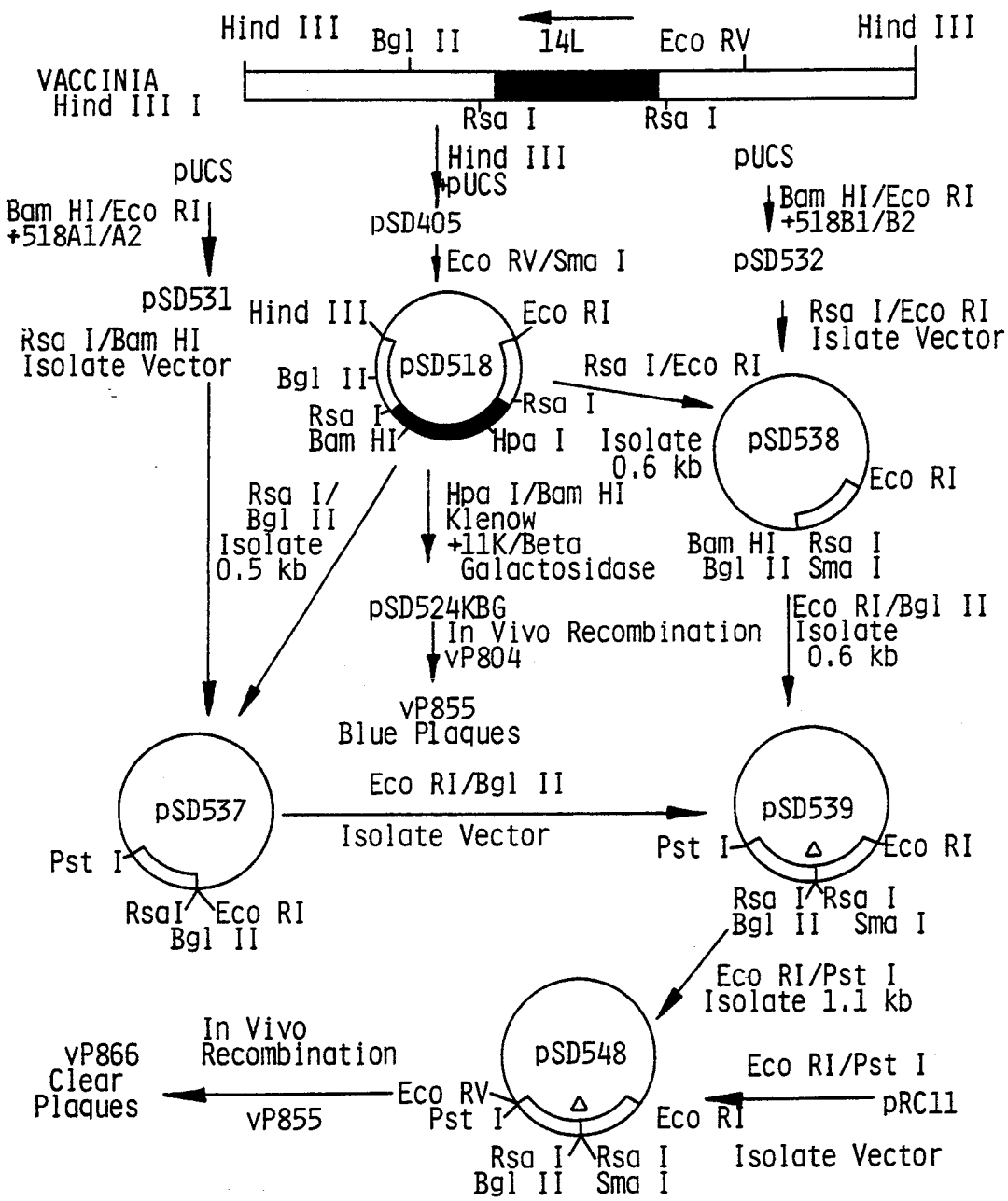
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63,875–70,367) cloned in pUCS. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of BglII
MPSYN82   5' TTTCTGTATATTTGCACCAATTTAGATCTTACTCAAAATATGTAACAATA 3'

The resulting plasmid, pMP409D, contains a unique BglII site inserted into the M2L deletion locus as indicated above. A 3.2 kb BamHI (partial)/BglII cassette containing the *E. coli* Betagalactosidase gene (52) under the control of the 11 kDa promoter (4) was inserted into pSD548.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of E. Coli polymerase. This 4.8 kb vector fragment was ligated with a 3.2 kb SmaI cassette containing the E. Coli Beta-galactosidase gene (52) under the control of the vaccinia 11 kDa promoter (4,42), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2

```
        BamHI    RsaI
518A1  5' GATCCTGAGTACTTTGTAATATAATGATATATATTTTCACTTTATCTCAT
518A2  3'       GACTCATGAAACATTATATTACTATATATAAAAGTGAAATAGAGTA

BglII          EcoRI
       TTGAGAATAAAAAGATCTTAGG       3'  518A1
       AACTCTTATTTTTCTAGAATCCTTAA   5'  518A2
``` forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2

```
        BamHI BglII   SmaI
518B1  5' GATCCAGATCTCCCGGGAAAAAAATTATTTAACTTTTCATTAATAGGGATTT
518B2  3'       GTCTAGAGGGCCCTTTTTTTAATAAATTGAAAAGTAATTATCCCTAAA

RsaI         EcoRI
       GACGTATGTAGCGTACTAGG       3'  518B1
       CTGCATACTACGCATGATCCTTAA   5'  518B2
``` forming plasmid pSD532. pSD532 was cut with RsI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid pSD539, the I4L ORF (pos. 65,047-67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, , a pUC derivative from which all Beta-galactosidase sequences have been removed and replaced with a polylinker region (9). pSD539 was cut with EcoRI/PstI and the 1.2 kb fragment isolated. This fragment was ligated into pRC11, cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (11) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

EXAMPLE 7

INSERTION OF A RABIES GLYCOPROTEIN G GENE INTO NYVAC

The gene encoding rabies glycoprotein G under the control of the vaccinia H6 promoter (61,62) was inserted into TK deletion plasmid pSD513. pSD513 is identical to plasmid pSD460 (FIG. 1) except for the presence of a polylinker region.

Figure 7:
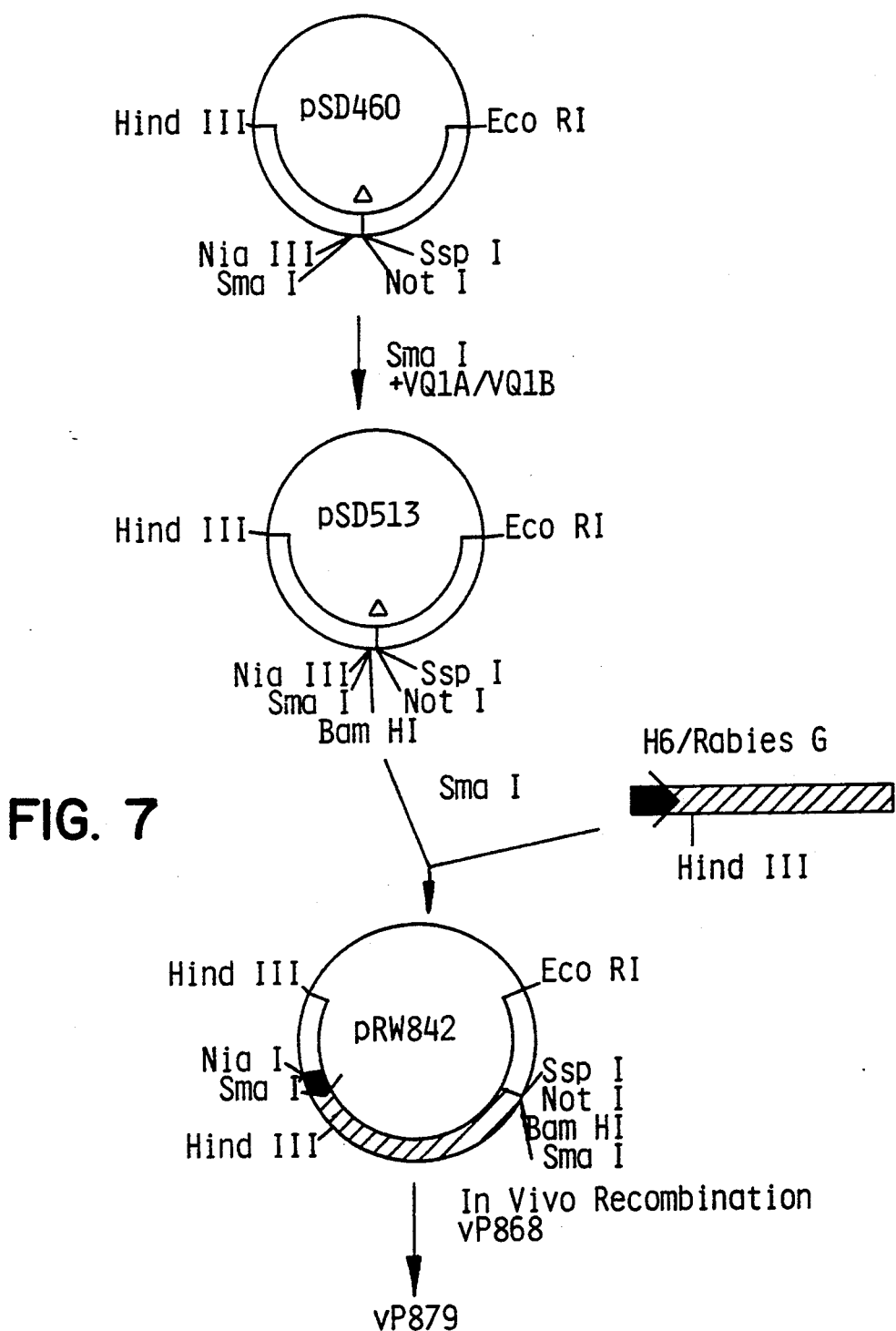
FIG. 7 schematically shows a method for the construction of plasmid pRW842 for insertion of rabies glycoprotein G gene into the TK deletion locus and generation of recombinant vaccinia virus vP879.

Referring now to FIG. 7, the polylinker region was inserted by cutting pSD460 with SmaI and ligating the plasmid vector with annealed synthetic oligonucleotides VQ1A/VQ1B

```
       SmaI   BglII    XhoI    PstI    NarI    BamHI
VQ1A  5' GGGAGATCTCTCGAGCTGCAGGGCGCCGGATCCTTTTTCT  3'
VQ1B  3' CCCTCTAGAGAGCTCGACGTCCCGCGGCCTAGGAAAAAGA  5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (61,62). The resulting plasmid was designated pRW842. pRW842 was used as donor plasmid for recombination with NYVAC rescuing virus (vP866). Recombinant vaccinia virus vP879 was identified by plaque hybridization using $^{32}$p-labelled DNA probe to rabies glycoprotein G coding sequences.

The modified recombinant viruses of the present invention provide advantages as recombinant vaccine vectors. The attenuated virulence of the vector advantageously reduces the opportunity of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

REFERENCES

1. Altenburger, W., C-P. Suter and J. Altenburger, Archives Virol. 105, 15–27 (1989).
2. Behbehani, A.M., Microbiological Reviews 47, 455–509 (1983).
3. Bergoin, M. and S. Dales, In *Comparative Virologly*, pp. 169–205 (edited by K. Maramorosch and E. Kurstak, Academic Press, New York) (1971)
4. Bertholet, C., R. Drillien and R. Wittek, Proc. Natl. Acad. Sci. 82, 2096–2100 (1985)
5. Buller, R. M. L., G. L. Smith, K. Cremer, A. L. Notkins and B. Moss, Nature 317, 813–815 (1985)
6. Child, S. J., G. J. Palumbo, R. M. L. Buller and D. E. Hruby, Virology 174, 625–629 (1990)
7. Clewell, D. B., J. Bacteriol 110, 667–676 (1972).
8. Clewell, D. B. and D. R. Helinski, Proc. Natl Acad. Sci. USA 62, 1159–1166 (1969).
9. Colinas, R. J., R. C. Condit and E. Paoletti, Virus Research 18, 49–70 (1990).
10. Drillien, R., F. Koehren and A. Kirn, Virology 111, 488–499 (1981).
11. Engelke, D. R., P. A. Hoener and F. S. Collins, Proc. Natl. Acad Sci USA 85, 544–548 (1988).
12. Funahashi, S., T. Sato and H. Shida, J. Geno Virol. 35–47 (1988).
13. Gillard, S., D. Spehner, R. Drillien and A. Kirn, Proc. Natl. Acad. Sci. USA 83, 5573–5577 (1986).
14. Goebel, S. J., Johnson, G.P., Perkus, M. E., Davis, S. W., Winslow, J. P. and E. Paoletti, Virology 179, 247–266 (1990).
15. Goebel, S. J., G. P. Johnson, M. E. Perkus, S. W. Davis, J.P. Winslow and E. Paoletti, Virology 179, 517–563 (1990).
16. Goldstein, D. J. and S. K. Weller, Virology 166, 41–51 (1988).
17. Guo, P., S. Goebel, S. Davis, M. E. Perkus, B. Languet, P. Desmettre, G. Allen and E. Paoletti, J. Virol. 63, 4189–4198 (1989 ).
18. GUO, P., S. Goebel, M. E. Perkus, J. Taylor, E. Norton, G. Allen, B. Languet, P. Desmettre and E. Paoletti, J. Virol. 64, 2399–2406 (1990).
19. Hruby, D. E. and L. A. Ball, J. Virol. 43, 403–409 (1982).
20. Hruby, D. E., R. A. Maki, D. B. Miller and L. A. Ball, Proc. Natl. Acad. Sci. USA 80, 3411–3415 (1983).
21. Ichihashi, Y. and Dales, S., Virology 46, 533–543 (1971).
22. Itamura, S., H. Iinuma, H. Shida, Y. Morikawa, K. Nerome and A. Oya, J Gen Virol 7, 2859–2865 (1990)
23. Jacobson, J. G., D. A. Leib, D. J. Goldstein, C. L. Bogard, P. A. Schaffer, S. K. Weller and D. M. Coen, Virology 173, 276–283 (1989).
24. Jamieson, A. T., G. A. Gentry and J. H. Subak-Sharpe, J. Gen. Virol. 24, 465–480 (1974).
25. Kato, S., M. Takahashi, S. Kameyama and J. Kamahora, Biken's 2, 353–363 (1959).
26. Kotwal, G. J., A. W. Hugin and B. Moss, Virology 171, 579–587 (1989).
27. Kotwal, G. J., S. N. Isaacs, R. McKenzie, M. M. Frank and B. Moss, Science 250, 827–830 (1990).
28. Kotwal, G. J. and B. Moss, Nature 335, 176–178 (1988).
29. Kotwal, G. J. and B. Moss, Virology 167, 524–537 (1988).
30. Kotwal, G. J. and B. Moss, J. Virol. 63, 600–606 (1989).
31. Lai, A. C.-K. and B. G.-T. Pogo, Virus Res. 12, 239–250 (1989) .
32. Mandecki, W., Proc. Natl. Acad. Sci. USA 83, 7177–7181 (1986) .
33. Maniatis, T., E. F. Fritsch and J. Sambrook, Cold Spring Harbor Laboratory, Cold Spring Harbor, N.Y. (1982).
34. Morgan, A. J., M. Mackett, S. Finerty, J. R. Arrand, F. T. Scullion and M. A. Epstein, J. Med. Virol. 25, 189–195 (1988).
35. MOSS, B., E. Winters and J. A. Cooper, J. Virol. 40, 387–395 (1981).
36. Paez, E., S. Dallo and M. Esteban, Proc. Natl. Acad. Sci. USA 82, 3365–3369 (1985).
37. Palumbo, G. J., D. J. Pickup, T. N. Fredrickson, L. J. Mcintyre and R. M. L. Buller, Virology 172, 262–273 (1989).
38. Panicali, D., S. W. Davis, S. R. Mercer and E. Paoletti, J. Virol, 37, 1000–1010 (1981).
39. Panicali, D. and E. Paoletti, Proc. Natl. Acad. Sci. USA 79, 4927–4931 (1982).
40. Patel, D. D. and D. J. Pickup, EMBO 6, 3787–3794 (1987).
41. Patel, D. D., C. A. Ray, R. P. Drucker, D. J. Pickup, Proc. Natl. Acad. Sci. USA 85, 9431–9435 (1988).
42. Perkus, M. E., S. J. Goebel, S. W. Davis, G. P. Johnson, K. Limbach, E. K. Norton and E. Paoletti, Virology 179, 276–286 (1990).
43. Perkus, M. E., S. J. Goebel, S. W. Davis, G. P. Johnson, E. K. Norton and E. Paoletti, Virology 180, 406–410 (1991).
44. Perkus, M. E., K. Limbach and E. Paoletti, J. Virol. 63, 3829–3836 (1989).
45. Perkus, M. E., D. Panicali, S. Mercer and E. Paoletti, Virology 152, 285–297 (1986).
46. Perkus, M. E., A. Piccini, B. R. Lipinskas and E. Paoletti, Science 229, 981–984 (1985).
47. Piccini, A., M. E. Perkus and E. Paoletti, Methods Enzymol. 153, 545–563 (1987).
48. Pickup, D. J., B. S. Ink, W. Hu, C. A. Ray and W. K. Joklik, Proc. Natl. Acad. Sci. USA 83, 7698–7702 (1986).
49. Pickup, D. J., B. S. Ink, B. L. Parsons, W. Hu and W. K. Joklik, Proc. Natl. Acad. Sci. USA 81, 6817–6821 (1984).

50. Sanger, F., S. Nicklen and A. R. Coulson, Proc. Natl. Acad. Sci. USA 74, 5463–5467 (1977).
51. Schmitt, J. F. C. and H. G. Stunnenberg, J. Virol. 62, 1889–1897 (1988)o
52. Shapira, S. K., Chou, J., Richaud, F. V. and Casadaban, M. J., Gene 25, 71–82 (1983).
53. Shida, H., Virology 150, 451–462 (1986).
54. Shida, H., Y. Hinuma, M. Hatanaka, M. Morita, M. Kidokoro, K. Suzuki, T. Maruyama, F. Takahashi-Nishimaki, Mo Sugimoto, R. Kitamura, T. Miyazawa and M. Hayami, J. Virol. 62, 4474–4480 (1988).
55. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
56. Slabaugh, M., N. Roseman, R. Davis and C. Mathews, J. Virol. 62, 519–527 (1988).
57. Stanberry, L. R., S. Kit and M. G. Myers, J. Virol. 55, 322–328 (1985).
58. Tabor, S. and C. C. Richardson, Proc. Natl. Acado Sci. USA 84, 4767–4771 (1987).
59. Tartaglia, J., S. Pincus and E. Paoletti, Critical Reviews in Immunology 10, 13–30 (1990).
60. Taylor, G., E. J. Stott, G. Wertz and A. Ball, J. Gen. Virol. 72, 125–130 (1991).
61. Taylor, J., R. Weinberg, L. Kawaoka, R. G. Webster and E. Paoletti, Vaccine 6, 504–506 (1988).
62. Taylor, J., R. Weinberg, B. Lanquet, P. Desmettre and E. Paoletti, Vaccine 6, 497–504 (1988).
63. Weir, J.P. and B. Moss, J. Virol. 46, 530–537 (1983).
64. Zhou, J., L. Crawford, L. McLean, X. Sun, M. Stanley, N. Almond and G. L. Smith, J. Gen. Virol. 71, 2185–2190 (1990).

What is claimed is:

1. A recombinant vaccinia virus wherein regions C7L-K1L, J2R, B13R+B14R, A26L, A56R and I4I have been deleted therefrom.

2. A recombinant vaccinia virus wherein the open reading frames:
for the thymidine kinase gene, the hemorrhagic region, the A type inclusion body region, the hemagglutinin gene, the host range gene region, and the large subunit, ribonucleotide reductase have been deleted therefrom.

3. The virus of claim 2 which is NYVAC.

4. The virus of claim 1 which is vP866.

5. A composition for inducing an immunological response in a host animal inoculated with said composition, said composition comprising the virus of claim 1 and a carrier.

6. A composition for inducing an immunological response in a host animal inoculated with said composition, said composition comprising the virus of claim 2 and a carrier.

7. A method of expressing a gene product in a cell cultured in vitro comprising introducing into the cell the virus of claim 1.

8. A method of expressing a gene product in a cell cultured in vitro comprising introducing into the cell the virus of claim 2.

* * * * *

UNITED STATES PATENT AND TRADEMARK OFFICE
CERTIFICATE OF CORRECTION

PATENT NO. : 5,364,773
DATED : November 15, 1994
INVENTOR(S) : Enzo Paoletti et al.

It is certified that error appears in the above-identified patent and that said Letters Patent is hereby corrected as shown below:

Claim 1, line 2 (column 25, line 55), change "I4I" to --I4L--.

Signed and Sealed this

Twenty-first Day of November, 1995

Attest:

BRUCE LEHMAN

Attesting Officer          Commissioner of Patents and Trademarks

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:1:

```
TAATTAACTA GCTACCCGGG                                                    20
```

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:2:

```
AATTCCCGGG TAGCTAGTTA ATTACATG                                           28
```

(2) INFORMATION FOR SEQ ID NO:3:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:3:

```
AGCTTCCCGG GTAAGTAATA CGTCAAGGAG AAAACGAAAC GATCTGTAGT TAGCGGCCGC        60
CTAATTAACT AAT                                                           73
```

(2) INFORMATION FOR SEQ ID NO:4:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:4:

```
ATTAGTTAAT TAGGCGGCCG CTAACTACAG ATCGTTTCGT TTTCTCCTTG ACGTATTACT        60
```

TACCCGGGA                                                                                           69

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

TTAGTTAATT AGGCGGCCGC                                                                               20

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:6:

CGATTACTAT GAAGGATCCG TT                                                                            22

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

AACGGATCCT TCATAGTAAT                                                                               20

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:8:

CGATTACTAG ATCTGAGCTC CCCGGGCTCG AGGGATCCGT T                                                        41

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:9:

AACGGATCCC TCGAGCCCGG GGAGCTCAGA TCTAGTAAT                                                           39

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:10:

GATCCGAATT CTAGCT                                                                                   16

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

AGCTAGAATT CG                                                                                                         12

( 2 ) INFORMATION FOR SEQ ID NO:12:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TATGAGTAAC TTAACTCTTT TGTTAATTAA AAGTATATTC AAAAAATAAG TTATATAAAT     60

AGATCTGAAT TCGTT                                                                                   75

( 2 ) INFORMATION FOR SEQ ID NO:13:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AACGAATTCA GATCTATTTA TATAACTTAT TTTTGAATA TACTTTTAAT TAACAAAAGA     60

GTTAAGTTAC TCA                                                                                       73

( 2 ) INFORMATION FOR SEQ ID NO:14:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AAAATGGGCG TGGATTGTTA ACTTTATATA ACTTATTTTT TGAATATAC                       49

( 2 ) INFORMATION FOR SEQ ID NO:15:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

ACACGAATGA TTTTCTAAAG TATTTGGAAA GTTTTATAGG TAGTTGATAG AACAAAATAC     60

ATAATTT                                                                                                       67

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TCTATCAACT ACCTATAAAA CTTTCCAAAT ACTTTAGAAA ATCATTCGTG T                 51

( 2 ) INFORMATION FOR SEQ ID NO:17:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

TGTAAAAATA AATCACTTTT TATACTAAGA TCTCCCGGGC TGCAGC    46

( 2 ) INFORMATION FOR SEQ ID NO:18:

( i ) SEQUENCE CHARACTERISTICS:
    ( A ) LENGTH: 66 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

GGCCGCTGCA GCCCGGGAGA TCTTAGTATA AAAAGTGATT TATTTTTACA AAATTATGTA    60

TTTTGT    66

( 2 ) INFORMATION FOR SEQ ID NO:19:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

TTTCTGTATA TTTGCACCAA TTTAGATCTT ACTCAAAATA TGTAACAATA    50

( 2 ) INFORMATION FOR SEQ ID NO:20:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

TGTCATTTAA CACTATACTC ATATTAATAA AAATAATATT TATT    44

( 2 ) INFORMATION FOR SEQ ID NO:21:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

GATCCTGAGT ACTTTGTAAT ATAATGATAT ATATTTCAC TTTATCTCAT TTGAGAATAA    60

AAAGATCTTA GG    72

( 2 ) INFORMATION FOR SEQ ID NO:22:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

AATTCCTAAG ATCTTTTTAT TCTCAAATGA GATAAAGTGA AAATATATAT CATTATATTA    60

CAAAGTACTC AG 72

( 2 ) INFORMATION FOR SEQ ID NO:23:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GATCCAGATC TCCCGGGAAA AAAATTATTT AACTTTTCAT TAATAGGGAT TTGACGTATG 60

TAGCGTACTA GG 72

( 2 ) INFORMATION FOR SEQ ID NO:24:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AATTCCTAGT ACGCATCATA CGTCAAATCC CTATTAATGA AAAGTTAAAT AATTTTTTC 60

CCGGGAGATC TG 72

( 2 ) INFORMATION FOR SEQ ID NO:25:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GGGAGATCTC TCGAGCTGCA GGGCGCCGGA TCCTTTTTCT 40

( 2 ) INFORMATION FOR SEQ ID NO:26:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

AGAAAAAGGA TCCGGCGCCC TGCAGCTCGA GAGATCTCCC 40